(12) United States Patent
Blake et al.

(10) Patent No.: US 9,763,432 B2
(45) Date of Patent: *Sep. 19, 2017

(54) RECOMBINANT CONSTRUCTS AND TRANSGENIC FLUORESCENT ORNAMENTAL FISH THEREFROM

(71) Applicant: YORKTOWN TECHNOLOGIES, LP, Austin, TX (US)

(72) Inventors: Alan Blake, Austin, TX (US); Richard Crockett, Wilton, CT (US); Jeffrey Essner, Ames, IA (US); Perry Hackett, Saint Paul, MN (US); Aidas Nasevicius, Tampa, FL (US)

(73) Assignee: GLOFISH LLC, Earth City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/041,253

(22) Filed: Feb. 11, 2016

(65) Prior Publication Data

US 2017/0006843 A1  Jan. 12, 2017

Related U.S. Application Data

(63) Continuation of application No. 14/057,333, filed on Oct. 18, 2013, now Pat. No. 9,271,478, which is a continuation of application No. 13/663,210, filed on Oct. 29, 2012, now Pat. No. 8,581,025, which is a continuation of application No. 12/577,467, filed on Oct. 12, 2009, now Pat. No. 9,295,237, which is a continuation of application No. 11/839,364, filed on Aug. 15, 2007, now Pat. No. 7,700,825.

(60) Provisional application No. 60/842,721, filed on Sep. 7, 2006, provisional application No. 60/838,006, filed on Aug. 16, 2006.

(51) Int. Cl.
 *A01K 67/027* (2006.01)
 *C07K 14/435* (2006.01)
 *C12N 15/85* (2006.01)
 *G06Q 99/00* (2006.01)

(52) U.S. Cl.
 CPC ........ *A01K 67/0275* (2013.01); *A01K 67/027* (2013.01); *C07K 14/43595* (2013.01); *C12N 15/8509* (2013.01); *G06Q 99/00* (2013.01); *A01K 2217/05* (2013.01); *A01K 2217/052* (2013.01); *A01K 2217/206* (2013.01); *A01K 2227/40* (2013.01); *A01K 2267/0393* (2013.01); *C12N 2830/008* (2013.01)

(58) Field of Classification Search
 CPC .............................................. A01K 67/0275
 See application file for complete search history.

(56) References Cited

U.S. PATENT DOCUMENTS

| | | |
|---|---|---|
| 2004/0117866 A1 | 6/2004 | Tsai |
| 2004/0143864 A1 | 7/2004 | Gong et al. |
| 2004/0216179 A1 | 10/2004 | Tsai |
| 2010/0050280 A1 | 2/2010 | Blake et al. |
| 2010/0145889 A1 | 6/2010 | Blake et al. |

OTHER PUBLICATIONS

"Mouse fast skeletal muscle SR calcium ATPase [Mus musculus]," Database EMBL, Database Accession No. CAA4762, Apr. 18, 2005.
Ben et al., "Cloning and tissue expression of 6-pyruvoyl tetrahydropterin synthase and xanthine dehydrogenase from Poecilia reticulata," *Mar. Biotechnol.*, 5:568-578, 2003.
Bourett et al., "Reef coral fluorescent proteins for visualizing fungal pathogens," *Fungal Genet. Biol.*, 37(3):211-220, 2002.
Clontech Laboratories, Inc., www.clontech.com, 2005.
CLONTECHniques, "Living Colors™ DsRed2," Jul. 2001.
Curtin et al., "Bidirectional promoter interference between two widely used internal heterologous promoters in a late-generation lentiviral construct," *Gene Therapy*, 15:384-390, 2008.
Du et al., "Growth Enhancement in Transgenic Atlantic Salmon by the Use of an "All Fish" Chimeric Growth Hormone Gene Construct ," *Bio/Technology*, 10:176-181, 1992.
Finley et al., "Three-color imaging using fluorescent proteins in living zebrafish embryos," *Biotechniques*, 31(1):66-72, 2001.
Gong et al., "Development of transgenic fish for ornamental and bioreactor by strong expression of fluorescent proteins in the skeletal muscle," *Biochemical and Biophysical Research Communications*, 308:58-63, 2003.
Gross et al., "Molecular analysis and growth evaluation of northern pike (*Esox lucius*) microinjected with growth hormone genes," *Aquaculature*, 103:253-273, 1992.
Hadjantonakis et al., "Technicolour transgenics: imaging tools for functional genomics in the mouse," Nat. Rev. Genet., 4(8):613-625, 2003.
Higashijima et al., "High-frequency generation of transgenic zebrafish which reliably express GFP in whole muscles or the whole body by using promoters of zebrafish origin," *Developmental Biology*, 192:289-299, 1997.
Hirrlinger et al., "Expression of reef coral fluorescent proteins in the central nervous system of transgenic mice," *Mol. Cell. Neurosci.*, 30:291-303, 2005.
Inagaki et al., "The Tyrosinase Gene from Medakafish: Transgenic Expression Rescues Albino Mutation," *Pigment Cell*, 11:283-290, 1998.
International Search Report and Written Opinion, issued in International Application No. PCT/US07/76020, dated Sep. 18, 2008.
Ju et al., "Recapitulation of fast skeletal muscle development in zebrafish by transgenic expression of GFP under the mylz2 promoter," *Dev Dyn.*, 227(1):14-26, 2003.

(Continued)

*Primary Examiner* — Valarie Bertoglio
(74) *Attorney, Agent, or Firm* — Parker Highlander PLLC

(57) ABSTRACT

The present invention relates to the method and use of reef coral fluorescent proteins in making transgenic red, green and yellow fluorescent zebrafish. Preferably, such fluorescent zebrafish are fertile and used to establish a population of transgenic zebrafish and to provide to the ornamental fish industry for the purpose of marketing. Thus, new varieties of ornamental fish of different fluorescence colors from a novel source are developed.

18 Claims, 6 Drawing Sheets

(56) References Cited

OTHER PUBLICATIONS

Lamason et al., "SLC24A5, a Putative Cation Exchanger, Affects Pigmentation in Zebrafish and Humans," *Science*, 310(5755):1782-1786, 2005.
Liu et al., "Development of expression vectors for transgenic fish," *Biotechnology*, 8:1268-1272, 1990.
M. Kinoshita, "Transgenic medaka with brilliant fluorescence in skeletal muscle under normal light," *Fisheries Science*, 70:645-649, 2004.
Matsumoto et al., "Expression and transmission of wild-type pigmentation in the skin of transgenic orange-colored variants of medaka (Oryzias latipes) bearing the gene for mouse tyrosinase," *Pigment Cell Res.*, 5:322-327, 1992.
Matz et al., "Fluorescent proteins from nonbioluminescent Anthozoa species," *Nat. Biotechnol.*, 17:969-973, 1999.
Miura et al., "Analysis of the tyrosinase gene of the Japanese pond frog, *Rana nigromaculata*: cloning and nucleotide sequence of the genomic DNA containing the tyrosinase gene and its flanking regions," *Jpn. J. Genet.*, 70:79-92, 1995.
Miyawaki, "Green fluorescent protein-like proteins in reef Anthozoa animals," *Cell Strum. Funct.*, 27(5):343-347, 2002.
Negishi et al., "Localization of sepiapterin reductase in pigment cells of Oryzias latipes," *Pigment Cell Res.*, 16:501-503, 2003.
Office Communication issued in International Application No. PCT/US07/76020, dated Jul. 9, 2008.
Office Communication issued in U.S. Appl. No. 11/839,364, dated Aug. 6, 2009.
Office Communication issued in U.S. Appl. No. 11/839,364, dated Sep. 17, 2009.
Office Communication issued in U.S. Appl. No. 11/839,364, dated Oct. 29, 2009.
Office Communication issued in U.S. Appl. No. 12/577,467, dated May 12, 2010.
Office Communication issued in U.S. Appl. No. 12/577,467, dated Nov. 22, 2010.
Office Communication issued in U.S. Appl. No. 12/577,467, dated Apr. 11, 2011.
Office Communication issued in U.S. Appl. No. 13/663,210, dated Feb. 28, 2013.
Office Communication issued in U.S. Appl. No. 12/577,467, dated Jan. 25, 2010.
Office Communication issued in U.S. Appl. No. 12/577,467, dated Aug. 20, 2013.
Office Communication issued in U.S. Appl. No. 12/577,467, dated Jul. 24, 2013.
Office Communication issued in U.S. Appl. No. 12/577,467, dated Oct. 16, 2013.
Office Communication issued in U.S. Appl. No. 14/057,333, dated Sep. 2, 2015.
Office Communication issued in U.S. Appl. No. 14/057,333, dated Jul. 29, 2015.
Office Communication issued in U.S. Appl. No. 14/057,333, dated Apr. 29, 2015.
Office Communication issued in U.S. Appl. No. 14/057,333, dated Oct. 2, 2014.
Office Communication issued in U.S. Appl. No. 12/577,467, dated May 18, 2015.
Office Communication issued in U.S. Appl. No. 12/577,467, dated May 30, 2014.
Parichy et al., "An orthologue of the kit-related gene fms is required for development of neural crest-derived xanthophores and a subpopulation of adult melanocytes in the zebrafish, *Danio rerio*," *Development*, 127:3031-3044, 2000.
Parichy et al., "Mutational Analysis of Endothelin Receptor b1 (rose) during Neural Crest and Pigment Pattern Development in the Zebrafish *Danio rerio*," *Developmental Biology*, 227:294-306, 2000.
Powers et al., "Electroporation: a method for transferring genes into the gametes of zebrafish (*Brachydanio rerio*), channel catfish (*Ictalurus punctatus*), and common carp (*Cyprinus carpio*)," *Mol. Marine Biol. Biotechnol.*, 1:301-308, 1992.
Sarkar et al., "Insulated piggyBac vectors for insect transgenesis," *BMC Biotechnol.*, 6(1):27, 2006.
Sin et al., "Gene transfer in chinook salmon (*Oncorhynchus tshawytsch*) by electroporating sperm in the presence of pRSV-lacZ DNA," *Aquaculature*, 117:57-69, 1993.
Smith, "Going Green," *Nat. Strum. Biol.*, 7:1089, 2000.
Szelei et al., "Liposome-mediated gene transfer in fish embryos," *Transgenic Res.*, 3:116-119, 1994.
Tolar et al., "Real-time in vivo imaging of stem cells following transgenesis by transposition," *Mol. Ther.*, 12(1):42-48, 2005.
Tsai et al., "Electroporation of sperm to introduce foreign DNA into the genome of loach (*Misgurnus anguillicaudatus*)," *Can. J. Fish Aquat. Sci.*, 52:776-787, 1995.
Wall et al., "The structural basis for red fluorescence in the tetrameric GFP homolog DsRed," *Nat. Struct. Biol.*, 7(12):1133-1138, 2000.
Wan et al., "Generation of two-color transgenic zebrafish using the green and red fluorescent protein reporter Genes *gfp* and *rfp*," *Marine Biotechnology*, 4:146-154, 2002.
Watson, "Production of Aquarium Fish," University of Florida, IFAS Extension, pp. 1-4, Jun. 1996.
Wenck et al., "Reef-coral proteins as visual, non-destructive reporters for plant transformation," *Plant Cell Rep.*, 22(4):244-251, 2003.
Wouters et al., "WZsGreen/+: a new green fluorescent protein knock-in mouse model for the study of KIT-expressing cells in gut and cerebellum," *Physiol. Genomics*, 2(3):412-421, 2005.
Xu et al., "Fast skeletal muscle-specific expression of a zebrafish myosin light chain 2 gene and characterization of its promoter by direct injection into skeletal muscle," *DNA Cell Biol.*, 18, 85-95, 1999.
Zelenin et al., "The delivery of foreign genes into fertilized fish eggs using high-velocity microprojectiles," *FEBS Lett.*, 287(1-2):118-120, 1991.
Zhao and Overbeek, "Tyrosinase-related protein 2 promoter targets transgene expression to ocular and neural crest-derived tissues," *Dev. Biol.*, 216:154-163, 1999.
Zhu and Zon, "Use of the DsRed fluorescent reporter in zebrafish," *Methods Cell Biol.*, 76:3-12, 2004.
Zhu et al., "Novel gene transfer into the fertilized eggs of gold fish (*Carassius auratus* L. 1758)," *Z. Angew. Ichthyol.*, 1:31-34, 1985.
Zhu et al., "Regulation of the lmo2 promoter during hematopoietic and vascular development in zebrafish," *Dev. Biol.*, 281(2):256-269, 2005.
Ziegler et al., "Development of the pteridine pathway in the zebrafish, *Danio rerio*," *J. Biol. Chem.*, 275:18926-18932, 2000.
Ziegler, "The pteridine pathway in zebrafish: regulation and specification during the determination of neural crest cell-fate," *Pigment Cell Res.*, 16:172-182, 2003.
Zou et al., "The Fugu tyrp1 promoter directs specific GFP expression in zebrafish: tools to study the RPE and the neural crest-derived melanophores," *Pigment Cell Res.*, 19:615-627, 2006.

Step 1. Using a restriction enzyme, the construct plasmid is opened, and the antibiotic resistance gene is separated from the desired DNA.

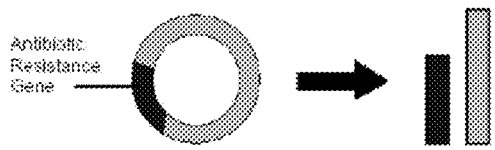

Step 2. The DNA fragments are collected and loaded into a gel.

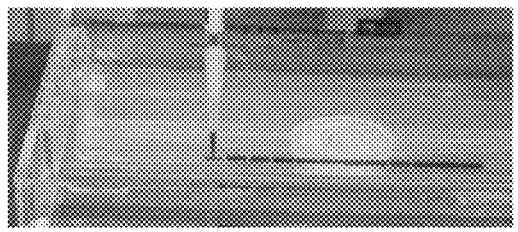

Step 3. Using an electric charge, the fragments of DNA are separated.

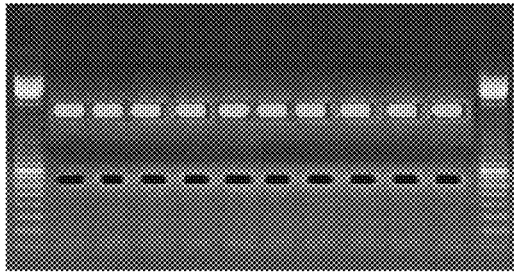

Step 4. The desired DNA, in our case, the green fluorescent protein gene construct, is collected and microinjected into a recently fertilized zebrafish embryo.

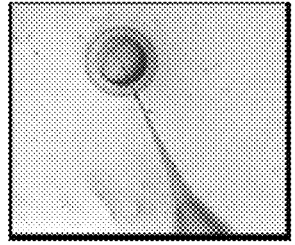

FIG. 6

RECOMBINANT CONSTRUCTS AND TRANSGENIC FLUORESCENT ORNAMENTAL FISH THEREFROM

The present application is a continuation of co-pending U.S. patent application Ser. No. 14/057,333, filed Oct. 18, 2013, which is a continuation of U.S. patent application Ser. No. 13/663,210, filed on Oct. 29, 2012, now U.S. Pat. No. 8,581,025, which is a continuation of co-pending U.S. patent application Ser. No. 12/577,467, filed on Oct. 12, 2009, which is a continuation of U.S. patent application Ser. No. 11/839,364 filed Aug. 15, 2007, now U.S. Pat. No. 7,700,825, which claims the benefit of U.S. Provisional Application Ser. Nos. 60/838,006, filed Aug. 16, 2006, and 60/842,721, filed Sep. 7, 2006, the disclosures of which are incorporated by reference herein in their entirety.

Pursuant to 37 C.F.R. 1.821(c), a sequence listing is submitted herewith as an ASCII compliant text file named "GLOFP0011USC6.txt", created on Jan. 22, 2016 and having a size of ~23 kilobytes. The content of the aforementioned file is hereby incorporated by reference in its entirety.

BACKGROUND OF THE INVENTION

1. Field of the Invention

This invention relates to transgenic gene constructs with fish gene promoters and heterologous genes for generation of transgenic fish, particularly fluorescent transgenic fish.

2. Description of Related Art

Transgenic technology involves the transfer of a foreign gene into a host organism enabling the host to acquire a new and inheritable trait. The technique was first developed in mice by Gordon et al. (1980). They injected foreign DNA into fertilized eggs and found that some of the mice developed from the injected eggs retained the foreign DNA. Applying the same technique, Palmiter et al. (1982) introduced a chimeric gene containing a rat growth hormone gene under a mouse heavy metal-inducible gene promoter and generated the first batch of genetically engineered supermice, which were almost twice as large as non-transgenic siblings. This work has opened a promising avenue in using the transgenic approach to provide to animals new and beneficial traits for livestock husbandry and aquaculture.

In addition to the stimulation of somatic growth for increasing the gross production of animal husbandry and aquaculture, transgenic technology also has many other potential applications. First, transgenic animals can be used as bioreactors to produce commercially useful compounds by expression of a useful foreign gene in milk or in blood. Many pharmaceutically useful protein factors have been expressed in this way. For example, human 1-antitrypsin, which is commonly used to treat emphysema, has been expressed at a concentration as high as 35 mg/ml (10% of milk proteins) in the milk of transgenic sheep (Wright et al., 1991). Similarly, the transgenic technique can also be used to improve the nutritional value of milk by selectively increasing the levels of certain valuable proteins such as caseins and by supplementing certain new and useful proteins such as lysozyme for antimicrobial activity (Maga and Murray, 1995). Second, transgenic mice have been widely used in medical research, particularly in the generation of transgenic animal models for human disease studies (Lathe and Mullins, 1993). More recently, it has been proposed to use transgenic pigs as organ donors for xenotransplantation by expressing human regulators of complement activation to prevent hyperacute rejection during organ transplantation (Cozzi and White, 1995). The development of disease resistant animals has also been tested in transgenic mice (e.g. Chen et al., 1988).

Fish are also an intensive research subject of transgenic studies. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing "superfish". While a majority of early attempts used heterologous growth hormone genes and promoters and failed to produce gigantic superfish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The zebrafish, *Danio rerio*, is a new model organism for vertebrate developmental biology. As an experimental model, the zebrafish offers several major advantages such as easy availability of eggs and embryos, tissue clarity throughout embryogenesis, external development, short generation time and easy maintenance of both the adult and the young. Transgenic zebrafish have been used as an experimental tool in zebrafish developmental biology. However, for the ornamental fish industry the dark striped pigmentation of the adult zebrafish does not aid in the efficient display of the various colors that are currently available in the market. More recently, Lamason et al. (2005) in their report showed that the Golden zebrafish carry a recessive mutation in the slc24a5 gene, a putative cation exchanger, and have diminished number, size and density of melanosomes which are the pigmented organelles of the melanocytes and hence are lightly pigmented as compared to the wild type zebrafish. The availability of the Golden zebrafish for transgenesis with fluorescent proteins would result in better products for the ornamental fish industry as it would allow for a better visualization of the various colors.

Green fluorescent protein (GFP) is a useful tool in the investigation of various cellular processes. The GFP gene was isolated from the jelly-fish *Aqueous victoria*. More recently, various other new fluorescent protein genes have been isolated from the Anthozoa class of coral reefs (Matz et al., 1999) called DsRed, red fluorescent protein gene; ZsGreen, green fluorescent protein gene and ZsYellow, yellow fluorescent protein gene. The novel fluorescent proteins encoded by these genes share 26-30% identity with GFP (Miyawaki, 2002). These are bright fluorescent proteins and each emits a distinct wavelength. They are physicochemically very stable, extremely versatile, emitting strong visible fluorescence in a variety of cell types and display exceptional photostability and hence fluoresce over extended periods of time. Because of their distinct spectra, they can be used in combination. The crystal structure of the DsRed protein suggests that the chromofore is located on a central α-helical segment embedded within a tightly folded β-barrel and that the DsRed protein forms tetramers in vivo (Wall et al., 2000).

Coral reef fluorescent proteins have broad application in research and development. The red fluorescent protein, DsRed, has been used as a reporter in the transgenic studies involving various animal model systems: for example, filamentous fungi (Eckert et al., 2005, Mikkelsen et al., 2003); ascidian (Zeller et al., 2006); zebrafish (Zhu et al., 2005, Zhu et al., 2004, Gong et al., 2003, Finley et al., 2001); *xenopus* (Werdien et al., 2001); insect (Cho et al., 2006, Handler et al., 2001, Horn et al., 2002); *drosophila* (Barolo et al., 2004); silkworm (Royer et al., 2005); mouse (Schmid et al., 2006, Vintersten et al., 2004); rat (Sato et al., 2003); and plants (Wenek et al., 2003). It has also been used a marker in imaging studies in stem cells (Tolar et al., 2005, Long et al., 2005) and mouse (Long et al., 2005, Hadjantonakis et al., 2003). Green fluorescent protein, ZsGreen, has been used as a transformation marker in insects (Sarkar et al., 2006), knock-in mouse model for the study of KIT expressing cells (Wouters et al., 2005) and as reporters for plant transformation (Wenck et al., 2003). Yellow fluorescent protein, ZsYellow, has been used a reporter for plant transformation (Wenck et al., 2003) and for visualizing fungal pathogens (Bourett et al., 2002). All of these transgenic experiments have aimed at developing newer markers and reporters for transgenesis; however, progress in the field of ornamental fish industry has been limited.

SUMMARY OF THE INVENTION

In certain embodiments, the present invention concerns making recombinant constructs and transgenic fluorescent fish and providing such fish to the ornamental fish industry. The term recombinant construct is used to mean recombinant DNA constructs having sequences which do not occur in nature or exist in a form that does not occur in nature or exist in association with other materials that do not occur in nature. The term transgenic has historically been used in many contexts with various meanings. In the embodiments of this invention transgenic is understood to mean genetic material artificially introduced into the genome of an organism. An organism incorporating such genetic material, or progeny to which this genetic material was passed, would be considered a transgenic organism. Such transgenic organisms may also, in certain embodiment, be referred to generally as a genetically modified organism (GMO), which is defined as an organism whose genetic material has been altered using the genetic engineering techniques generally known as recombinant DNA technology. This modified DNA is then transferred into an organism preferably resulting in the expression of modified or novel traits. The term "GMO" does not cover organisms whose genetic makeup has been altered by conventional cross breeding or by "mutagenesis" breeding, as these methods predate the discovery of the recombinant DNA techniques. Technically, however, such techniques are by definition genetic modification. The term fluorescent is used to mean an entity that absorbs light of one wavelength and emits at a different wavelength.

Specific embodiments of the present invention are directed to methods of making transgenic fluorescent fish having one sequence from a group of SEQ ID NO:1, SEQ ID NO:2, SEQ ID NO:3, SEQ ID NO:4 and SEQ ID NO:5, as well as transgenic fish developed by such methods. Thus, a transgenic zebrafish having integrated into its germ line cell DNA a transgenic construct comprising one or more of SEQ ID NO:1 through SEQ ID NO:5 is also included as part of the invention. Further more, the invention provides transgenic zebrafish egg and/or sperm cells comprising a sequence according to SEQ ID NO:1 through SEQ ID NO:5 integrated in its/their genome(s). In certain aspects of the invention, two or more sequences from a group of SEQ ID NO:1, SEQ ID NO:2, SEQ ID NO:3, SEQ ID NO:4 and SEQ ID NO:5 are used in one zebrafish. In a specific aspect, SEQ ID NO:1 and SEQ ID NO:2 are used in the same fish and SEQ ID NO:3 and SEQ ID NO:5 are used in the same fish. In preferred embodiments, it is contemplated that the transgenic fluorescent fish are fertile transgenic fluorescent fish.

In another preferred embodiment, the fish for use with the disclosed constructs and methods is the Golden zebrafish. Zebrafish skin color is determined by pigment cells in their skin, which contain pigment granules called melanosomes. The number, size and density of the melanosomes per pigment cell influence the color of the fish skin. Golden zebrafish have diminished number, size, and density of melanosomes and hence have lighter skin when compared to the wild type zebrafish. Golden zebrafish have a mutation in slc24a5 gene, rendering the fish skin lighter or less pigmented (Lamason et al., 2005).

In another embodiment of the invention, a method for making transgenic fluorescent fish is provided comprising at least the following steps: a) preparing a vector which has a transgenic fluorescence expression cassette comprising one sequence from a group of SEQ ID NO:1, SEQ ID NO:2, SEQ ID NO:3, SEQ ID NO:4 and SEQ ID NO:5, or two or more sequences from a group of SEQ ID NO:1, SEQ ID NO:2, SEQ ID NO:3, SEQ ID NO:4 and SEQ ID NO:5 are used in combination, specifically, SEQ ID NO:1 and SEQ ID NO:2 are used together and SEQ ID NO:3 and SEQ ID NO:5 are used together; b) making the transgenic zebrafish using the vectors; and, c) selecting transgenic zebrafish that fluoresce by monitoring fluorescence under a light of appropriate wavelength. The transgenic expression cassette has a set of transcriptional regulatory motifs, herein referred to as a promoter, which may be from the host species (herein referred to as a homologous promoter) or from another species (herein referred to as a heterologous promoter), heterologous fluorescent gene, and appropriate RNA-processing and/or translational enhancing motif. The term promoter as used herein refers to the DNA elements that direct and regulate transcription. For instance, the zebrafish fast skeletal muscle myosin light chain promoter and carp β-actin promoter may be used according to the invention.

In certain specific embodiments there are provided methods to use multiple vectors to express at least one fluorescent protein in order to enhance expression. The preferred mode is to make a transgenic fish comprising in its genome a first fluorescent transgene under the control of a ubiquitous fish promoter, and a second fluorescent transgene under the control of a tissue specific fish promoter. The ubiquitous fish promoter is selected from the group consisting of those transcriptional motifs that direct gene expression in most cells, and more preferably in all cells; they are also preferably promoters for 'housekeeping genes', such as tubulin, ribosomal protein, and actin genes. The tissue specific fish promoter is selected from the group consisting of those transcriptional motifs that are active in specific cells of differentiated tissues such as muscle, brain, liver, blood and eyes. In a preferred embodiment, the tissue specific fish promoter is muscle specific. As used herein, a promoter drives expression "specifically" in a tissue if the level of expression is at least 5-fold, preferably at least 10-fold higher, more preferably at least 50-fold higher in that tissue than in any other tissue.

More than one construct can be injected into the fish embryos simultaneously. For example, in the present invention, both Red zebrafish 1 and Green zebrafish 1 incorporate more than one transgenic expression cassettes, with one being a ubiquitous promoter, and the other being a strong muscle promoter. In particular, Red zebrafish 1 incorporates the cassettes represented by FIG. 1 and FIG. 4, and Green zebrafish 1 incorporates the cassettes represented by FIG. 2 and FIG. 5. While the present invention incorporates only the transgenic insert cassettes shown in the Figures, it is understood that multiple transgenic insert cassettes of any type can be simultaneously injected into a fish embryo from any species.

The steps involved in making the transgenic fish further involve isolation and separation of the transgenic expression cassette from the vector backbone to remove any gene encoding antibiotic resistance (e.g., ampicillin or kanamycin) and origin of replication. In a preferred mode, a suitable promoter would be expected to drive stable and consistent expression throughout the life of the fish. To achieve such stable expression, it is necessary to choose a promoter that is known to drive stable and consistent expression throughout the life of the fish. For example, a promoter that drives expression only during the six months of the life of the fish would not be suitable for use. Examples of suitable promoters may be selected from the group consisting of those for housekeeping genes, such as tubulin, ribosomal protein, and actin gene promoters.

It is also preferred to use regulatory elements, for example, RNA processing and translational enhancing elements in the transgenic insert cassette to produce a transgenic fluorescent, ornamental fish. The RNA processing signals, preferably, are one or more polyadenylation signals and/or one or more introns. Since introns are sequences between exons, the presence of an intron automatically indicates the presence of two exons. Accordingly, two introns indicate the presence of three exons, and so on. The carp beta-actin intron used in SEQ ID 2 and SEQ ID 5 is an example of such an intron, and the untranslated carp beta-actin exon used in SEQ ID 2 and SEQ ID 5 is an example of such an exon. Exons and introns other than carp beta-actin can be used as well. The translational enhancing elements, preferably, are 5' untranslated leader sequences of 40-200 nucleotides, and more preferably untranslated leader sequences of 40-70 nucleotides. It is known that the presence of introns in primary transcripts can increase expression, possibly by causing the transcript to enter the processing and transport system for mRNA. It is also preferred that the intron be homologous to the host species, and more preferably homologous to the expression sequences used (that is, that the intron be from the same gene that some or all of the expression sequences are from).

The disclosed transgene constructs preferably include other sequences which improve expression from, or stability of, the construct. For example, including a polyadenylation signal on the constructs encoding a protein ensures that transcripts from the transgene will be processed and transported as mRNA. The identification and use of polyadenylation signals in expression constructs is well established. It is preferred that efficient polyadenylation signals, such as those derived from viruses, be used in the transgenic constructs, and more preferred to use at least two polyadenylation signals, which more preferably are two copies of SV40 polyadenylation sequence.

It is also a subject of this invention to disclose expression of the fluorescent protein gene only in chromatophores. There are several types of chromatophores found in animals: melanophores (black), xanthophores (yellow), erythrophores (red), cyanophores (blue), leucophores (white) and iridophores (reflective). Different species of fish contain all types of chromatophores, usually a subset of them in different combinations. Zebrafish contain melanophores, xantophores and iridophores. These different cell types express specific genes, characteristic only for them or specific for a subset of chromatophores. In a preferred embodiment, promoters of these specific genes fused to fluorescent protein open reading frames (ORFs) can be used to visualize specific chromatophores. The specific genes can be roughly divided into two major groups: regulatory proteins and biosynthesis enzymes, involved in specific pigment synthesis. Expression of regulatory proteins usually is at lower level than that of biosynthesis enzymes therefore use of promoters of biosynthesis enzymes are most preferred.

The heterologous fluorescent gene may be, for example, a gene encoding DsRed2, ZsGreen1 and ZsYellow1. The heterologous fluorescent gene may also be any variation or mutation of these genes, encoding fluorescent proteins including green fluorescent protein (GFP), enhanced green fluorescent protein (eGFP), yellow fluorescent protein (YFP), enhanced yellow fluorescent protein (eYFP), blue fluorescent protein (BFP), enhanced blue fluorescent protein (eBFP), cyan fluorescent protein (CFP) and enhanced cyan fluorescent protein (eCFP) or any of the proteins listed in Table 4, or any variation or mutation thereof, or any other fluorescence proteins. The steps involved in making the transgenic fish also involve introduction of the transgenic expression cassette into the zebrafish embryos or zebrafish embryonic stem cells. Such embryos and cells are allowed to grow and mature into adult fish and then they are screened for the presence of the transgenic expression cassette using the various molecular biology methods described in the detailed description section and/or by functional biochemical assays such as assaying for the activity of the introduced fluorescent gene by exposing the said fish to light of appropriate wavelength and/or by visibly inspecting the fish and observing the expression. Transgenic fluorescent fish are further bred to insure transmission of the transgenic expression cassette via the germ cells of a fish as further described in this application.

The present invention also provides a method to obtain a progenitor of a new line of fluorescent transgenic fish, and a population therefrom, which exhibit strong visible fluorescence. Strong visible fluorescence means that a person with 20/20 vision (i.e., average vision) will be able to distinguish between the fluorescent fish in question and a non-fluorescent fish of the same species at a distance of at least 5 feet in a lighted office, with a preferred distance of at least 10 feet in a lighted office, and a more preferred distance of at least 15 feet in a lighted office, and an even more preferred distance of at least 20 feet in a lighted office, with the illumination level defined in Table 5. One can observe all transgenic fluorescent fish from a particular population that exhibit strong visible fluorescence under the various lighting conditions and select the fish that exhibits the highest level of visible fluorescence of the fluorescent protein. Selected fish with strong visible fluorescence are monitored and their progeny selected continuously to ensure stability of expression and maintenance of strong visible fluorescence. Thus a new line of fish that exhibit strong visible fluorescence is created for further breeding.

Transgenic fish made by the present disclosure will emit red, yellow-green and yellow-orange fluorescence under light of distinct wavelengths and hence will be unique and attractive to the ornamental fish industry. In yet another embodiment of the invention, a method of making the transgenic fish available to the consumer by a grower or a commercial distributor through a retailer for sale to the public. In such embodiment, the fish may also be sold by the grower or commercial distributor to a regional wholesale distributor, who will then sell to a retailer for sale to the public. The fluorescent transgenic fish are also useful for the development of a biosensor system and as research models for embryonic studies such as cell lineage, cell migration, cell and nuclear transplantation, cell-cell interaction in vivo, etc.

Transgenic zebrafish comprising an expression cassette according to the invention may be homozygous or heterozygous with respect to the expression cassette. In some preferred aspects, fish for use in breeding of transgenic zebrafish of the invention will be homozygous for an expression cassette. Homozygous fish bred with fish lacking an expression cassette (e.g., Golden zebrafish) will in nearly all cases produce 100% heterozygous offspring. Likewise, transgenic fish for commercial retail will preferably be heterozygous for an expression cassette. Furthermore in some very specific aspects a transgenic fish of the invention comprises the specific integration event of the Red fluorescent expression cassette described in Example 3.

In certain specific embodiments there are provided transgenic fluorescent zebrafish comprising specific transgenic integration events. These fish are of particular interest since, for example, they embody an esthetically pleasing level of protein fluorescence. Thus, in some embodiments there is provided a transgenic zebrafish comprising a chromosomally integrated expression cassette encoding a DsRed2 gene wherein the zebrafish comprises the Red zebrafish 1 transformation event, sperm comprising said Red zebrafish 1 transformation event having been deposited as ECACC accession no. 06090403. In some other aspects, there is provided a transgenic zebrafish comprising a chromosomally integrated expression cassette encoding a ZsGreen1 gene wherein the zebrafish comprises the Green zebrafish 1 transformation event, sperm comprising said Green zebrafish 1 transformation event having been deposited as ECACC accession no. 06090401. In still other aspects, there is provided a transgenic zebrafish comprising a chromosomally integrated expression cassette encoding a ZsYellow1 gene wherein the zebrafish comprises the Yellow zebrafish 1 transformation event, sperm comprising said Yellow zebrafish 1 transformation event having been deposited as ECACC accession no. 06090402. As described above, transgenic fish comprising these specific transgenic events may be homozygous or heterozygous for transgene, and in some cases may comprise more than one of the transgenic events, although it is preferred to have only one integration location for any given transgenic modification. Eggs, sperm and embryos comprising these specific transgenic events are also included as part of the instant invention. Each of the three foregoing transgenic events were deposited with the European Collectin of Cell Cultures (ECACC), Porton Down, Salisbury, Wiltshire, SP4 OJG, UK, on Sep. 4, 2006, under the provisions of the Budapest Treaty.

Any of the fluorescence genes noted in this application may be used in similar embodiments of this invention. Embodiments discussed in the context of a method and/or composition of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings are part of the present specification and are included to further demonstrate certain aspects of the present invention. The invention may be better understood by reference to the drawing in combination with the detailed description of specific embodiments presented herein.

N1 (Clontech) and inserted into EcoRI and SpeI sites. The 440-bp 3'UTR/poly(A) sequence encoding tandem SV40 polyadenylation signals was PCR amplified from pK-SV40 (A)x2 and clone into SpeI and NotI sites. XhoI, XmnI and NotI restriction sites were used to isolate the expression construct from the vector backbone. Also shown is the ampicillin (Amp) resistance gene in the backbone of the pBluescript plasmid. The total length of the recombinant plasmid pzMLC-ZsYellow1-SV40x2 is 6043 bp.

Figure 4:
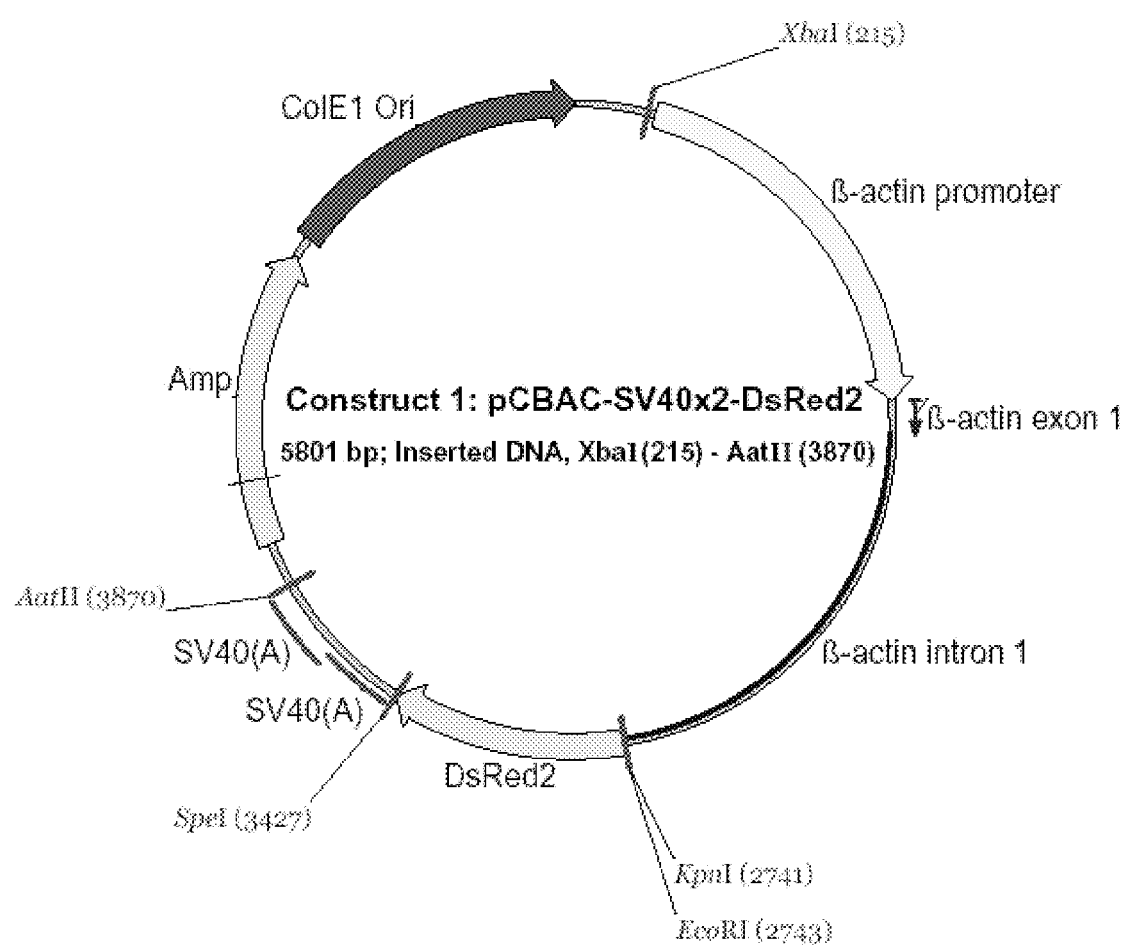

FIG. 4: The figure shows a schematic map of the transgenic construct, pCBAC-DsRed2-SV40x2. The 2.5-kb common carp beta-actin enhancer/promoter sequence, beta-actin exon-1 and beta-actin intron-1 was amplified by PCR from pFV7b vector and cloned into XbaI and KpnI restriction sites. The 684 bp DsRed2 fluorescent protein CDS was amplified by PCR from pDsRed2-N1 (Clontech) and inserted into EcoRI and SpeI sites. The 443-bp 3'UTR/poly (A) sequence encoding tandem SV40 polyadenylation signals sequence encoding tandem SV40 signal was PCR amplified from pK-SV40(A)x2 and cloned into SpeI and AatII sites. XbaI and AatII restriction sites were used to isolate the expression construct from the vector backbone. Also shown is the ampicillin (Amp) resistance gene in the backbone of the pBluescript plasmid. The total length of the recombinant plasmid pCBAC-DsRed2-SV40x2 is 5801 bp.

Figure 5:
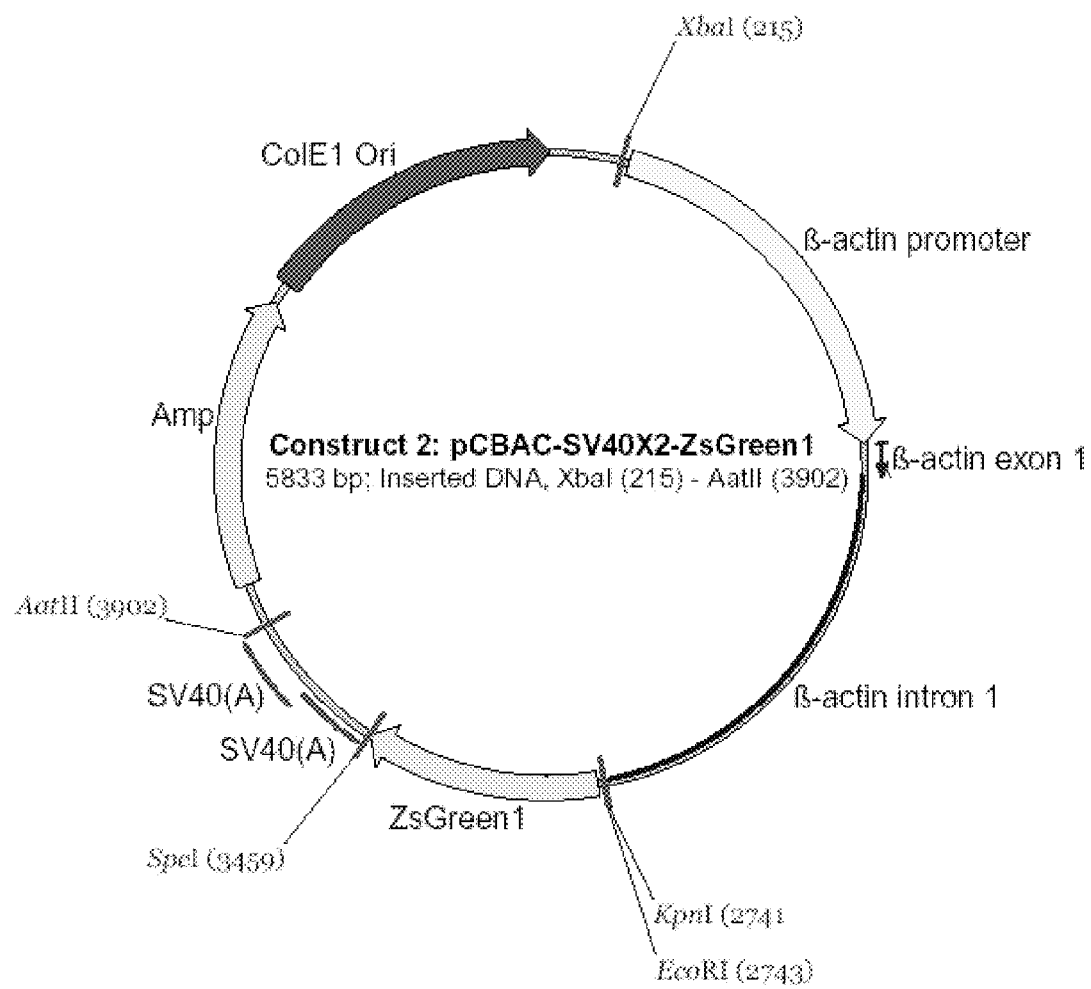

FIG. 5: The figure shows a schematic map of the transgenic construct, pCBAC-ZsGreen1-SV40x2. The 2.5-kb carp beta-actin enhancer/promoter sequence, beta-actin exon 1 and beta-actin intron 1 was amplified by PCR from pFV7b vector and cloned into XbaI and KpnI restriction sites. The 716 bp ZsGreen1 fluorescent protein CDS was amplified by PCR from pZsGreen1-N1 (Clontech) and inserted into EcoRI and SpeI sites. The 443 bp 3'UTR/poly (A) sequence encoding tandem SV40 polyadenylation signals sequence encoding tandem SV40 signal was PCR amplified from pK-SV40(A)x2 and cloned into SpeI and AatII sites. XbaI and AatII restriction sites were used to isolate the expression construct from the vector backbone. Also shown is the ampicillin (Amp) resistance gene in the backbone of the pBluescript plasmid. The total length of the recombinant plasmid pCBAC-ZsGreen1-SV40x2 is 5833 bp.

FIG. 6: Transgenic Construct purification and injection process. The Figure depicts step by step the process of transgenic construct purification and injection. Step 1 illustrates separation of the plasmid backbone sequence with the antibiotic resistance gene and origins of replication (pUC ori and fl(−) ori) (on left) and the expression construct (on right). Step 2 and 3 show the method of purification of the expression construct by loading and electrophoretic separation of the DNA fragments on an agarose gel. The antibiotic resistance gene and origins of replication (pUC ori and fl(−) ori) are below the expression construct on the gel. Step 4 exemplifies the process of microinjection of the gel-purified expression construct in to the fertilized zebrafish embryos.

DETAILED DESCRIPTION OF THE INVENTION

Transgenic Constructs

The present invention encompasses transgenic constructs which are genetic material artificially introduced into fish to produce a transgenic fish. The manner of introduction, and, often, the structure of a transgenic construct, render such a transgenic construct an exogenous construct. Although a transgenic construct can be made up of any assembly of nucleic acid sequences, for use in the disclosed transgenic fish it is preferred that the transgenic constructs combine regulatory elements operably linked to a sequence encoding one or more proteins. The methods and protocols for designing and making transgenic constructs are well known to those skilled in the art and can be found, for example, in Sambrook et al., 2001; Sambrook et al., 1989 and U.S. Pub No. 2004/0143864 A1, all of which are hereby incorporated by reference in their entireties.

To develop successful transgenic fish with a predictable pattern of transgenic expression, the first step is to make the appropriate genetic construct. The genetic construct generally comprises three portions: transcriptional regulators comprising a promoter, a gene and appropriate RNA-processing and/or translational enhancing motif. The gene promoter would determine where, when and under what conditions the gene is expressed. The gene contains protein coding portions that determine the protein to be synthesized and thus the biological function. The gene might also contain intron sequences which can affect mRNA processing or which might contain transcription regulatory elements. The RNA processing signals may include: one or more polyadenylation signals and one or more introns. Among the three portions, it is preferable to use a promoter that drives strong expression. The promoter may be a homologous promoter or it may be a heterologous promoter.

A promoter drives expression "predominantly" in a tissue if expression is at least 2-fold, preferably at least 5-fold higher in that tissue compared to a reference tissue. A promoter drives expression "specifically" in a tissue if the level of expression is at least 5-fold, preferably at least 10-fold higher, more preferably at least 50-fold higher in that tissue than in any other tissue. A ubiquitous promoter drives expression in most tissues, and preferably in all tissues.

Recombinant DNA Constructs

Recombinant DNA constructs comprising one or more of the DNA sequences described herein and an additional DNA sequence are also included within the scope of this invention. These recombinant DNA constructs usually have sequences which do not occur in nature or exist in a form that does not occur in nature or exist in association with other materials that do not occur in nature. The DNA sequences described as constructs or in vectors above are "operably linked" with other DNA sequences. DNA regions are operably linked when they are functionally related to each other. Generally, operably linked means contiguous (or in close proximity to).

The disclosed transgenic constructs preferably include other sequences that improve expression from, or stability of, the construct. For example, including a polyadenylation signal on the constructs encoding a protein ensures that mRNA transcripts from the transgene will be efficiently translated as protein. The identification and use of polyadenylation signals in expression constructs is well established. It is preferred that defined and efficient polyadenylation signals, such as those derived from viruses, be used in the transgenic constructs, and more preferred to use at least two polyadenylation signals, which more preferably are two copies of SV40 polyadenylation sequence.

In certain specific embodiments there are provided methods to use multiple vectors to express at least one fluorescent protein in order to enhance expression. The preferred mode is to make a transgenic fish comprising in its genome a first fluorescent transgene under the control of a ubiquitous fish promoter, and a second fluorescent transgene under the control of a tissue specific fish promoter. In a preferred embodiment, the tissue specific fish promoter is muscle specific. The ubiquitous fish promoter and the muscle specific promoter are, for example, selected from Table 1 below. In the Table 1, any promoter marked with an "X" is confirmed available at this time, with any unmarked promoter, or any other promoter of interest, available preferably through the following steps: following the database searching instructions provided in detail below, conducting a literature search, and sequencing the gene and promoter of interest through methods that are well know by artisans in the field.

The provided Table 1 of muscle-specific and ubiquitous promoters constitutes only a small portion of publicly available promoters. An extensive list of genes with expression of interest (e.g., muscle-specific expression) can be found using NCBI protein database server (www at ncbi.nlm.nih.gov/sites/entrez?db=Protein). For example, in order to find mouse genes expressed in skeletal muscles a search string "mouse skeletal muscle" can be used. The search results in a list of proteins including their accession number (e.g., CAA47621) and their name (e.g., mouse fast skeletal muscle SR calcium ATPase). In order to find genome information (e.g., sequence) of the found proteins, Ensembl Genome Browser (www at ensembl.org/index.html) can be employed, using the accession number ((e.g., CAA47621) as a search string. The search output will yield Ensembl gene ID (e.g., ENSMUSG00000030730), gene homologues in other organisms (e.g., zebrafish—*Danio rerio*), as well as genomic information of the gene of interest, including genomic sequence of the coding region (introns and exons), as well as genomic DNA sequence surrounding the coding sequence (e.g., "[Exon info]" link directs a user to the sequence information). Gene promoters are located upstream (5' flanking sequence) from the coding sequence, often within several (e.g., five) kilobases. In addition, some regulatory sequences can be found in introns of the gene of interest—these regulatory sequences are usually omitted from constructing tissue-specific gene expression "drivers" due to complexity of locating them. It is to be understood that the same approach can be used starting with "zebrafish skeletal muscle" or "medaka skeletal muscle" or any other species. The searcher may then continue the search as suggested above to find the genome and promoter information of interest. It is also to be understood that methods similar to the one described for searching the database referenced above can be used to search other existing sequence databases, as well as databases that are likely to be compiled in the future.

Table 2, below, is a partial list of Ensembl gene ID numbers of mouse and zebrafish skeletal muscle specific and ubiquitous genes found using this approach.

TABLE 1

Muscle specific and ubiquitous promoters for fish expression

| Gene promoter | Zebrafish | Fugu | Tetraodon | Medaka | Xenopus | Rat | Mouse | Dog | Bovine |
|---|---|---|---|---|---|---|---|---|---|
| Muscle specific | | | | | | | | | |
| Muscle creatine kinase | X | X | X | X | X | X | X | X | X |
| MyoD | X | X | X | X | X | X | X | X | X |
| Myogenin | X | X | X | X | X | X | X | X | X |
| Desmin | X | X | | | | X | X | X | X |
| Muscle enolase-3 | X | | X | | | X | X | | X |
| beta-sarkoglycan | X | X | X | X | X | X | X | X | X |
| Dystrophin | X | X | X | X | X | X | X | | X |
| Serum response factor | X | X | X | X | X | X | X | X | X |
| a-tropomyosin | X | X | X | X | X | X | X | X | X |
| Myosin heavy chain | X | X | | X | X | X | X | X | X |
| Mitoctiondrial creatine kinase 2 | X | X | X | X | | | X | X | X |
| Myosin light chain | X | X | X | X | X | X | X | X | X |
| Ca2+ transporting ATPase(fast twitch 1) | X | | | | | | X | | |
| skeletal Troponin T1(slow) | X | | | | | | X | | |
| Tropomodulin 4 | X | | | | | | X | | |
| Four and a half LIM domains 1 | X | | | | | | X | | |
| Fast-type myosin binding protein C | X | | | | | | X | | |
| Calsequestrin 1 | X | | | | | | X | | |
| Fast muscle troponin C2 | X | | | | | | X | | |
| Phosphorylase kinase alpha 1 | X | | | | | | X | | |
| Skeletal troponin I(fast 2) | X | | | | | | X | | |
| Ubiquitous | | | | | | | | | |
| EF-1 alpha | X | X | X | X | X | X | X | X | X |
| Histone 2A ZA | X | X | X | X | | | X | X | X |
| Acidic ribosomal phosphoprotein PO (ARP) | X | X | X | X | X | | X | | |
| alpha-catenin | X | X | X | X | X | X | X | X | X |
| beta-catenin | | X | | X | X | X | X | X | X |
| gamma-catenin | | X | | X | X | X | X | X | X |
| Srb7 | X | X | | X | | X | X | X | X |
| Creatine kinase(mitochondrial 1) | X | | | | | | X | | |
| Ubiquitous Ca2+ transporting ATPase | X | | | | | | X | | |
| Ancient ubiquitous protein | X | | | | | | X | | |
| Ubiquitin specific peptidase 4 | X | | | | | | X | | |
| Acetyl-Coenzyme A acryltransferase 2 | X | | | | | | X | | |
| Monoglyceride lipase | X | | | | | | X | | |
| Splicing factor 3b subunit 1 | X | | | | | | X | | |
| Tubulin β5 | X | | | | | | X | | |
| Beta-Actin | | | | | | | | | |

TABLE 2

Ensembl IDs of Muscle Specific Promoters

MUSCLE CREATINE KINASE PROMOTERS

Zebrafish: (ENSDARG00000035327)
Fugu: (SINFRUG00000143294)
*Tetraodon*: (GSTENG00012956001)
Medaka: (ENSORLG00000000449)
*Xenopus tropicalis*: (ENSXETG00000019108)
Rat: (ENSRNOG00000016837)
Mouse: (ENSMUSG00000030399)
Dog: (ENSCAFG00000004507)
Bovine: (ENSBTAG00000013921)

MYOD PROMOTERS

Zebrafish: (ENSDARG00000030110)
Fugu: (SINFRUG00000154785)
*Tetraodon*: (GSTENG00003954001)
Medaka: (ENSORLG00000000694)
*Xenopus tropicalis*: (ENSXETG00000001320)
Rat: (ENSRNOG00000011306)
Mouse: (ENSMUSG00000009471)
Dog: (ENSCAFG00000009066)
Bovine: (ENSBTAG00000002216)

MYOGENIN PROMOTERS

Zebrafish: (ENSDARG00000009438)
Fugu: (SINFRUG00000121801)
*Tetraodon*: (GSTENG00013986001)
Medaka: (ENSORLG00000015906)
*Xenopus tropicalis*: (ENSXETG00000001704)
Rat: (ENSRNOG00000030743)
Mouse: (ENSMUSG00000026459)
Dog: (ENSCAFG00000010309)
Bovine: (ENSBTAG00000006030)

DESMIN PROMOTERS

Zebrafish: (ENSDARG00000058656)
Fugu: (SINFRUG00000121939)
*Xenopus tropicalis*: (ENSXETG00000019275)
Rat: (ENSRNOG00000019810)
Mouse: (ENSMUSG00000026208)
Dog: (ENSCAFG00000015475)
Bovine: (ENSBTAG00000005353)

MUSCLE ENOLASE 3 BETA PROMOTERS

Zebrafish: (ENSDARG00000039007)
*Tetraodon*: (GSTENG00003809001)
Rat: (ENSRNOG00000004078)
Mouse: (ENSMUSG00000060600)
Bovine: (ENSBTAG00000005534)

BETA-SARCOGLYCAN PROMOTERS

Zebrafish: (ENSDARG00000052341)
Fugu: (SINFRUG00000123612)
*Tetraodon*: (GSTENG00032779001)
Medaka: (ENSORLG00000000171)
*Xenopus tropicalis*: (ENSXETG00000011676)
Rat: (ENSRNOG00000002135)
Mouse: (ENSMUSG00000029156)
Dog: (ENSCAFG00000002001)
Bovine: (ENSBTAG00000014601)

DYSTROPHIN PROMOTERS

Zebrafish: (ENSDARG00000008487)
Fugu: (SINFRUG00000144815)
*Tetraodon*: (GSTENG00024870001)
Medaka: (ENSORLG00000020638)
*Xenopus tropicalis*: (ENSXETG00000012391)
Rat: (ENSRNOG00000003667)
Mouse: (ENSMUSG00000045103)
Bovine: (ENSBTAG00000008254)

SERUM RESPONSE FACTOR PROMOTERS

Zebrafish: (ENSDARG00000053918)
Fugu: (SINFRUG00000162928)
*Tetraodon*: (GSTENG00025109001)
Medaka: (ENSORLG00000013036)
*Xenopus tropicalis*: (ENSXETG00000018511)
Rat: (ENSRNOG00000018232)
Mouse: (ENSMUSG00000015605)
Dog: (ENSCAFG00000001829)
Bovine: (ENSBTAG00000012777)

ALPHA-TROPOMYOSIN PROMOTERS

Zebrafish: (ENSDARG00000033683)
Fugu: (SINFRUG00000130484)
*Tetraodon*: (GSTENG00015950001)
Medaka: (ENSORLG00000012326)
Rat: (ENSRNOG00000018184)
Mouse: (ENSMUSG00000032366)
Dog: (ENSCAFG00000016966)
Bovine: (ENSBTAG00000005373)

MYOSIN HEAVY CHAIN PROMOTERS

Zebrafish: (ENSDARG00000035437)
Fugu: (SINFRUG00000135173)
Medaka: (ENSORLG00000001985)
*Xenopus tropicalis*: (ENSXETG00000023939)
Rat: (ENSRNOG00000031400)
Mouse: (ENSMUSG00000033196)
Dog: (ENSCAFG00000023926)
Bovine: (ENSBTAG00000007090)

MITOCHONDRIAL CREATINE KINASE (SARCOMERIC, CKMT2) PROMOTERS

Zebrafish: (ENSDARG00000035079)
Fugu: (SINFRUG000000160265)
*Tetraodon*: (GSTENG00028607001)
Medaka: (ENSORLG00000000769)
Mouse: (ENSMUSG00000021622)
Dog: (ENSCAFG00000008707)
Bovine: (ENSBTAG00000001003)

MYOSIN LIGHT CHAIN PROMOTERS

Zebrafish: (ENSDARG00000017441)
Fugu: (SINFRUG00000125026)
*Tetraodon*: (GSTENG00015855001)
Medaka: (ENSORLG00000015981)
*Xenopus tropicalis*: (ENSXETG00000006917)
Rat: (ENSRNOG00000013262)
Mouse: (ENSMUSG00000061816)
Dog: (ENSCAFG00000013875)
Bovine: (ENSBTAG00000009707)

While this approach will result in a great number of sequences, additional points should be considered to generate a list of strong promoters. For example, abundant structural genes (e.g., myosin) or abundant enzymes (e.g., SR calcium ATPase) are likely to yield strong promoters. This screening can easily be performed by an artisan in the field.

Figure 1:
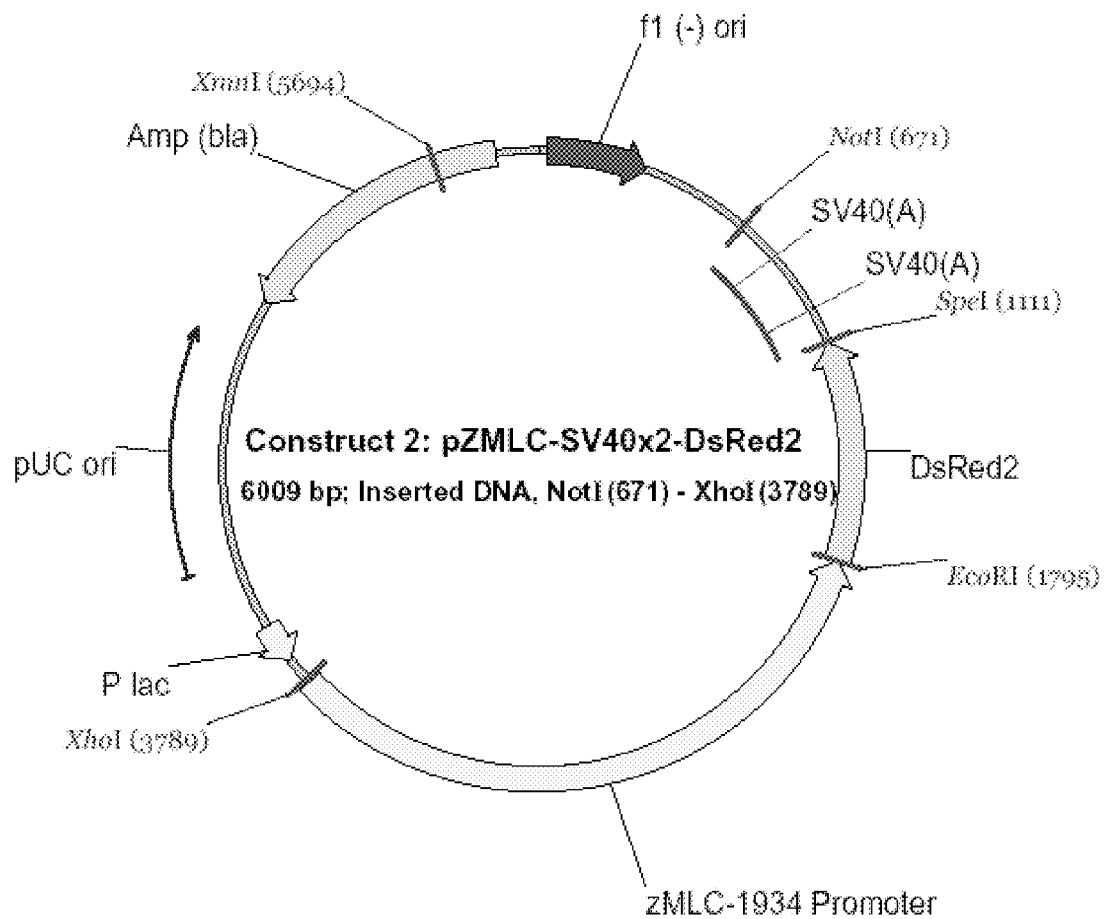
FIG. 1: The figure shows a schematic map of the transgenic construct, pZMLC-DsRed2-SV40x2. The 2.1-kb eukaryotic promoter sequence zMLC-1934 promoter was amplified by PCR from pMLC vector and cloned into XhoI and EcoRI restriction sites. The 684 bp DsRed2 fluorescent protein CDS was amplified by PCR from pDsRed2-N1 (Clontech) and inserted into EcoRI and SpeI sites. The 440-bp 3'UTR/poly(A) sequence encoding tandem SV40 polyadenylation signals was PCR amplified from pK-SV40 (A)x2 and cloned into SpeI and NotI sites. XhoI, XmnI and NotI restriction sites were used to isolate the expression construct from the vector backbone. Also shown is the ampicillin (Amp, formally known as beta-lactamase (bla)) resistance gene in the backbone of the pBluescript plasmid. The total length of the recombinant plasmid pzMLC-DsRed2-SV40x2 is 6009 bp.
Figure 2:
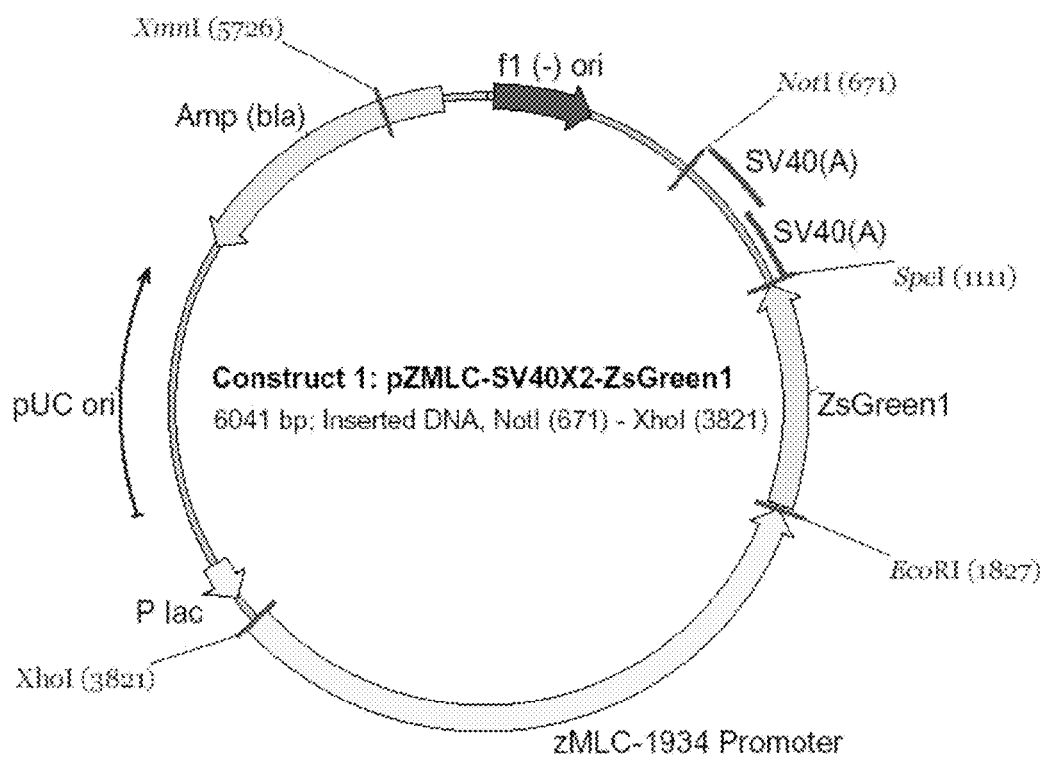
FIG. 2: The figure shows a schematic map of the transgenic construct, pZMLC-ZsGreen1-SV40x2. The 1.9-kb eukaryotic promoter sequence zMLC-1934 promoter was amplified by PCR from pMLC vector and cloned into XhoI and EcoRI restriction sites. The 716 bp ZsGreen1 fluorescent protein CDS was amplified by PCR from pZsGreen1-N1 (Clontech) and inserted into EcoRI and SpeI sites. The 440-bp 3'UTR/poly(A) sequence encoding tandem SV40 polyadenylation signals was PCR amplified from pK-SV40 (A)x2 and clone into SpeI and NotI sites. XhoI, XmnI and NotI restriction sites were used to isolate the expression construct from the vector backbone. Also shown is the ampicillin (Amp) resistance gene in the backbone of the pBluescript plasmid. The total length of the recombinant plasmid pzMLC-ZsGreen1-SV40x2 is 6041 bp.
Figure 3:
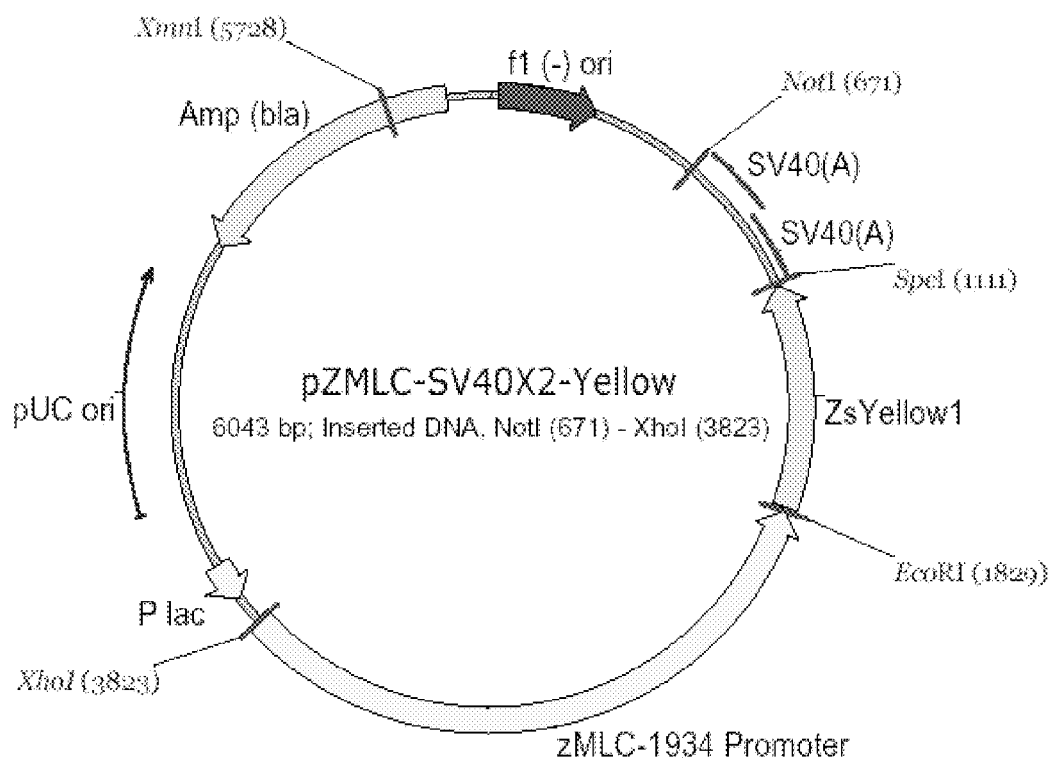
FIG. 3: The figure shows is a schematic map of the transgenic construct, pZMLC-ZsYellow1-SV40x2. The 1.9-kb eukaryotic promoter sequence zMLC-1934 promoter was amplified by PCR from pMLC vector and cloned into XhoI and EcoRI restriction sites. The 718 bp ZsYellow1 fluorescent protein CDS was amplified by PCR from pZsYellow1-

Preferably more than one construct with different promoters can be injected into the fish embryos simultaneously. For example, in the present invention, both Red zebrafish 1 and Green zebrafish 1 incorporate more than one transgenic expression cassette, with one being a ubiquitous promoter, and the other being a strong muscle promoter. In particular, Red zebrafish 1 incorporates the cassettes represented by FIG. 1 and FIG. 4, and Green zebrafish 1 incorporates the cassettes represented by FIG. 2 and FIG. 5. While the present invention incorporates only the transgenic insert cassettes shown in the Figures, it is understood that multiple transgenic insert cassettes of any type can be simultaneously injected into a fish embryo from any species.

It is also a subject of this invention to disclose expression of the fluorescent protein gene specifically in chromatophores. Chromatophores are pigment-containing and light-reflecting cells found in animals. There are several types of chromatophores: melanophores (black), xanthophores (yellow), erythrophores (red), cyanophores (blue), leucophores (white) and iridophores (reflective). Of those, only melanophores, called melanocytes, are found in higher vertebrates, such as mammals. Different species of fish contain all types of chromatophores, usually a subset of them in different combinations. Zebrafish contain melanophores, xantophores and iridophores. These different cell types express specific genes, characteristic only for them or specific for a subset of known promoters to choose from. With respect to iridophores, a few specific genes have been isolated (for example, endothelin receptor b1 Ednrb1). The least known chromatophores are the cyanophores—neither the nature of their pigment, nor specification pathway of the cells per se is known.

TABLE 3

Chromatophore-specific expressed genes in fishes

| Chromatophore | Protein | Synth/Reg | Organism | Reference |
|---|---|---|---|---|
| Iridophore | ednrb1 (endothelin receptor b1) | Reg | Zebrafish | Parichy et al, Developmental Biology 227, 294-306 (2000) |
| Xanthophore | xanthine dehydrogenase | Synth | Guppy (*Poecilia reticulata*); Zebrafish | Ben et al, Mar Biotechnol (NY). 2003 November-Dececember; 5(6): 568-78. Epub 2003 Aug. 21; Parichy et al, Developmental Biology 227, 294-306 (2000) |
| | sepiapterin reductase | Synth | medaka (*Oryzias latipes*) | Negishi et al, Pigment Cell Res. 2003 October; 16(5): 501-3 |
| | Xanthine oxidoreductase | Synth | | |
| | Fms/Csf1 | Reg | zebrafish | Ziegler, Pigment Cell Res. 2003 June; 16(3): 172-82; Ziegler et al, J Biol Chem. 2000 Jun. 23; 275(25): 18926-32; Parichy et al, Development 127, 3031-3044 (2000) |
| Melanophores | Mitf | Reg | Zebrafish | |
| | kit | Reg | Zebrafish | |
| | tyrp1 | Synth | zebrafish, fugu | Zou et al, Pigment Cell Res. 2006 December; 19(6): 615-27 |
| | tyrosinase | Synth | *rana nigromaculata* | Miura et al, Jpn J Genet. 1995 February; 70(1): 79-92 |
| | tyrosinase | Synth | medaka | Inagaki et al, Pigment Cell Res. 1998 October; 11(5): 283-90 |
| | tyrosinase | Synth | Mouse in medaka | Matsumoto et al, Pigment Cell Res. 1992 November; 5(5 Pt 2): 322-7 |
| | trp2 (tyrosinase-related protein 2) | Synth | mouse | Zhao & Over beek, Dev Biol. 1999 Dec. 1; 216(1): 154-63 |
| | dopachrome tautomerase | Synth | | | chromatophores. For example, tyrosinase-related protein 1 (tyrp1) is found only in melanophores; ednrb1 is found in malenocytes and iridophores. Promoters of these specific genes fused to fluorescent protein open reading frames (ORFs) can be used to visualize specific chromatophores. For example, fugu tyrp1 promoter can be used to drive fluorescent protein expression in melanophores in zebrafish. The specific genes can be roughly divided into two major groups: regulatory proteins (for example, kit—a receptor tyrosine kinase, specific to melanophores) and biosynthesis enzymes, involved in specific pigment synthesis (for example, sepiapterin reductase, involved in yellow pigment synthesis in xanthophores). Expression of regulatory proteins usually is at lower level than that of biosynthesis enzymes therefore use of promoters of biosynthesis enzymes are most preferred. A chromatophore-specific gene expression is outlined in Table 3 below.

Of all chromatophores, melanophores have been studied most extensively (due to their relevance to human biology). Therefore, a lot is known about transcription factors specific to melanophores, as well as biosynthesis enzymes involved in melanin synthesis in different classes of organisms, ranging from lower vertebrates to humans. The next best characterized chromatophores are the Xanthophores, for which a number of genes have been isolated, yielding, a number of It is also known that the presence of introns in primary transcripts can increase expression, possibly by causing the transcript to enter the processing and transport system for mRNA. It is preferred that the intron be homologous to the host species, and more preferably homologous to the expression sequences used (that is, that the intron be from the same gene that some or all of the expression sequences are from). The use and importance of these and other components useful for transgenic constructs are discussed in Palmiter et al. (1991); Sippel et al. (1992); Kollias and Grosveld (1992); and Clark et al. (1993).

The steps involved in making the transgenic fish further involve isolation and separation of the transgenic expression cassette from the vector backbone to remove the gene encoding antibiotic (e.g., ampicillin or kanamycin) resistance and origin of replication. In a preferred mode, a suitable promoter is chosen which is expected to drive stable expression throughout the life of the fish. To achieve such stable expression, it is necessary to choose a promoter that is known to drive stable and consistent expression throughout the life of the fish. For example, a promoter that drives expression only during the six months of the life of the fish would not be suitable to achieve stable expression throughout the life of the fish.

The heterologous fluorescent gene may be, for example, a gene encoding DsRed2, ZsGreen1 and ZsYellow1. The heterologous fluorescent gene may also be any variation or mutation of these genes, encoding fluorescent proteins including green fluorescent protein (GFP), enhanced green fluorescent protein (eGFP), yellow fluorescent protein (YFP), enhanced yellow fluorescent protein (eYFP), blue fluorescent protein (BFP), enhanced blue fluorescent protein (eBFP), cyan fluorescent protein (CFP) and enhanced cyan fluorescent protein (eCFP) or any of the proteins listed in Table 4, below, or any variation or mutation thereof, or any other fluorescence proteins. The steps involved in making the transgenic fish also involve introduction of the transgenic expression cassette into the zebrafish embryos or zebrafish embryonic stem cells. Such embryos and cells are allowed to grow and mature into adult fish and then they are screened for the presence of the transgenic expression cassette using the various molecular biology methods described in the detailed description section and/or by functional biochemical assays such as assaying for the activity of the introduced fluorescent gene by exposing the said fish to light of appropriate wavelength and/or by visibly inspecting the fish and observing the expression. Transgenic fluorescent fish are further bred to insure transmission of the transgenic expression cassette to the germ cells of a fish as further described in this application.

TABLE 4

Fluorescent Proteins ("FP") with their Maximum Excitation and Emission Wavelengths

| FP | Excitation max (nm) | Emission max (nm) |
| --- | --- | --- |
| AmCyan1 | 458 | 489 |
| ZsGreen1 | 493 | 505 |
| ZsYellow1 | 529 | 539 |
| DsRed2 | 563 | 582 |
| DsRed-Express | 557 | 579 |
| AsRed2 | 576 | 592 |
| HcRed1 | 588 | 618 |
| mPlum | 590 | 649 |
| mCherry | 587 | 610 |
| tdTomato | 554 | 581 |
| mStrawberry | 574 | 596 |
| J-Red | 584 | 610 |
| DsRed-monomer | 556 | 586 |
| mOrange | 548 | 562 |
| mKO | 548 | 559 |
| MCitrine | 516 | 529 |
| Venus | 515 | 528 |
| Ypet | 517 | 530 |
| EYFP | 514 | 527 |
| Emerald | 487 | 509 |
| EGFP | 488 | 507 |
| CyPet | 435 | 477 |
| mCFPm | 433 | 475 |
| Cerulean | 433 | 475 |
| T-Sapphire | 399 | 511 |

The sequences of the DNAs which are useful in the invention are set forth in the attached Sequence Listing.

The sequence listed herein as SEQ ID NO:1 is the transgenic fluorescence expression cassette having zebrafish fast skeletal muscle specific myosin light chain (zMLC) promoter, DsRed2 (a red fluorescent protein gene from Anthozoa, a reef coral), and two copies of the SV40 polyadenylation sequence. The sequence listed in SEQ ID NO:1 is the complementary sequence to the coding DNA strand.

The sequence listed herein as SEQ ID NO:2 is the transgenic fluorescence expression cassette having carp ubiquitous β-actin enhancer/promoter, DsRed2 (a red fluorescent protein gene from Anthozoa, a reef coral), and two copies of the SV40 polyadenylation sequence. The first exon and intron of β-actin has been incorporated in the SEQ ID NO:2 to allow for increased expression of the fluorescence protein gene.

The sequence listed herein as SEQ ID NO:3 is the transgenic fluorescence expression cassette having zebrafish fast skeletal muscle specific myosin light chain (zMLC) promoter, ZsGreen1 (a green fluorescent protein gene from Anthozoa, a reef coral), and two copies of the SV40 polyadenylation sequence. The sequence listed in SEQ ID NO:3 is the complementary sequence to the coding DNA strand.

The sequence listed herein as SEQ ID NO:4 is the transgenic fluorescence protein expression cassette having zebrafish fast skeletal muscle specific myosin light chain (zMLC) promoter, ZsYellow1 (a yellow fluorescent protein gene from Anthozoa, a reef coral), and two copies of SV40 polyadenylation sequence. The sequence listed in SEQ ID NO:4 is the complementary sequence to the coding DNA strand.

The sequence listed herein as SEQ ID NO:5 is the transgenic fluorescence protein expression cassette having carp ubiquitous β-actin enhancer/promoter, ZsGreen1 (a green fluorescent protein gene from Anthozoa, a reef coral), and two copies of SV40 polyadenylation sequence. The first exon and intron of β-actin has been incorporated in the SEQ ID NO:5 to allow for increased expression of the fluorescence gene Chimeric Genes The present invention encompasses chimeric genes comprising a promoter described herein operatively linked to a heterologous gene. Thus, a chimeric gene can comprise a promoter of a zebrafish operatively linked to a zebrafish structural gene other than that normally found linked to the promoter in the genome. Alternatively, the promoter can be operatively linked to a gene that is exogenous to a zebrafish, as exemplified by the DsRed2 and other genes specifically exemplified herein. Furthermore, a chimeric gene can comprise an exogenous promoter linked to any structural gene not normally linked to that promoter in the genome of an organism.

Substitutions, Additions and Deletions

As possible variants of the above specifically exemplified polypeptides, the polypeptide may have additional individual amino acids or amino acid sequences inserted into the polypeptide in the middle thereof and/or at the N-terminal and/or C-terminal ends thereof so long as the polypeptide possesses the desired physical and/or biological characteristics. Likewise, some of the amino acids or amino acid sequences may be deleted from the polypeptide so long as the polypeptide possesses the desired physical and/or biochemical characteristics. Amino acid substitutions may also be made in the sequences so long as the polypeptide possesses the desired physical and biochemical characteristics. DNA coding for these variants can be used to prepare gene constructs of the present invention.

A nucleic acid sequence "encodes" or "codes for" a polypeptide if it directs the expression of the polypeptide referred to. The nucleic acid can be DNA or RNA. Unless otherwise specified, a nucleic acid sequence that encodes a polypeptide includes the transcribed strand, the hnRNA and the spliced RNA or the DNA representative thereof.

Degenerate Sequences

In accordance with degeneracy of genetic code, it is possible to substitute at least one base of the base sequence of a gene by another kind of base without causing the amino acid sequence of the polypeptide produced from the gene to be changed. Hence, the DNA of the present invention may also have any base sequence that has been changed by substitution in accordance with degeneracy of genetic code.

DNA Modification

The DNA is readily modified by substitution, deletion or insertion of nucleotides, thereby resulting in novel DNA sequences encoding the polypeptide or its derivatives. These modified sequences are used to produce mutant polypeptide and to directly express the polypeptide. Methods for saturating a particular DNA sequence with random mutations and also for making specific site-directed mutations are known in the art; see e.g. Sambrook et al., (1989).

Transgenic Fish

The disclosed constructs and methods can be used with any type of fish that is an egg-layer. It is preferred that fish belonging to species and varieties of fish of commercial value, particularly commercial value within the ornamental fish industry, be used. Such fish include but are not limited to catfish, zebrafish, medaka, carp, tilapia, goldfish, tetras, barbs, sharks (family cyprinidae), angelfish, loach, koi, glassfish, catfish, angel fish, discus, eel, tetra, goby, gourami, guppy, Xiphophorus, hatchet fish, Molly fish, or pangasius. A more complete list of ornamental fish species can be found in Table 5 below:

TABLE 5

Ornamental Fish Species

| Scientific Name | Common Name |
| --- | --- |
| Steatocranus casuarius | African Blockhead |
| Apistograma agassizi | Agassizi |
| Hyphessobrycon h axelrodi, sp | Albino Black Neon Tetra |
| Lamprophogus brichardi | Albino Bricardi Cichld |
| Paracheirodon innessi, sp. | Albino Brilliant Neon Tetra |
| Hemigrammus caudovitatus | Albino Buenos Aires Tetra |
| Hemigrammus erythrozonus | Albino Glow Light Tetra |
| Hemigrammus ocellifer | Albino Head Tail Light Tetra |
| Pelvicachromis pulcher | Albino Kribensis Cichlid |
| Aplochelius normani | Albino Lampeye |
| Hyphessobrycon pulchripinnis sp | Albino Lemon Tetra |
| Paracheirodon innessi | Albino Neon Tetra |
| Macropodus opercularis spp | Albino Paradise Fish |
| Pterophyllum scalare | Albino Red Eye Angel |
| Epalzeorhynchos frenatus | Albino Redfin Shark |
| Hem. Rhodostomus sp. | Albino Rummy Nose |
| Capoeta tetrazona | Albino Tiger Barb |
| Astronotus ocellatus | Albino Tiger Oscar |
| Tanichtys albonubes sp. | Albino White Cloud |
| Lepisosteus oculatus | Alligator Gar |
| Luciosoma spilopleura | Apollo Shark |
| Toxotes jaculatrix | Archer Fish |
| Xiphophorus variatus | Assorted Variatus |
| Badis badis | Badis Badis |
| Helostoma temmincki | Balloon Kissing Gourami |
| Corydoras metae | Bandit Corydoras |
| Pangasius sutchi | Bangkok Catfish |
| Ancistrus dolichopterus | Big-Fin Bristlenose Golden Longfin |
| Peocilia latipinna | Black Balloon Molly |
| Cichlasoma maculicauda | Black Belt Cichlid |
| Carrasius auratus | Black Butterfly Tail |
| Callochromis macrops | Black Eared Callochromis |
| Leptosoma Kitumba | Black Finned Slender Cichlid |
| Apteronotus albifrons | Black Ghost |
| Acanthopthalmus myersi | Black Kuhlii |
| Bogrichthys hypselopterus | Black Lancer |
| Hyphessobrycon h axelrodi | Black Neon Tetra |
| Nematobrycon palmeri spp | Black Palmeri |
| Megalamphodus megalopterus | Black Phantom |
| Rasbora trilineata | Black Scissor Tail Rasbora |
| Labeo chrysopekadion | Black Shark |
| Puntius filamentosus | Black Spot Barb |
| Rasbora agilis | Black Stripe Rasbora |
| Gymnocorymbus ternetzi | Black Tetra |
| Astyanax fas. mexicanus | Blind Cave Tetra |

TABLE 5-continued

Ornamental Fish Species

| Scientific Name | Common Name |
| --- | --- |
| Brachydanio kerri | Blue Danio |
| Inpaichtys kerri | Blue Emperor Tetra |
| Trichogaster trichopterus | Blue Gourami |
| Boehlkea fredcochui | Blue King Tetra |
| Xiphophorus maculatus | Blue Platy |
| Melanotaenia lacustris | Blue Rainbow |
| Poecilia reticulata | Blue Ribbon Guppy |
| Pseudotropheus zebra | Blue Zebra |
| Melanotaenia boesemani | Boesemani Rainbow |
| Gastromyzon punctulatus | Borneo Sucker |
| Datnoides microlepis | Borneo Tiger Fish |
| Paracheirodon innesi | Brilliant Diamond Head Neon |
| Rasbora birttani | Brittan'S Rasbora |
| Brachygobius doriae | Bumble Bee Goby |
| Anomalochromis thomasi | Butterfly Cichlid |
| Notesthes robusta | Butterfly Goby |
| Paracheirodon axelrodi | Cardinal Tetra - M |
| Nomorhampheus liemi | Celebes Halfbeak |
| Telmatherina ladigesi | Celebes Rainbow |
| Chaca bankanensis | Chaca - Chaca |
| Capoeta oligolepis | Checkered Barb |
| Capoeta titteya | Cherry Barb |
| Sphaerichthys osphromenoides | Chocolate Gourami |
| Clarias batracus | Clarias - Spotted |
| Epiplatys annulatus | Clown Killie/Rocket |
| Botia macracantha | Clown Loach |
| Haplochromis sp | Cobalt/Ice Blue Cichlid |
| Apistograma cacatuoides | Cockatoo Dwarf |
| Hyphessobrycon colombianus | Colombia Tetra |
| Phenacogrammus interruptus | Congo Tetra |
| Corydoras aeneus | Corydoras Albino |
| Corydoras panda | Corydoras Panda |
| Corydoras paleatus | Corydoras Peppered |
| Corydoras pigmy | Corydoras Pigmy |
| Corydoras rabauti | Corydoras Rabauti |
| Corydoras similis | Corydoras Similis |
| Corydoras sterbai | Corydoras Sterbai |
| Synodontis multipunctatus | Cuckoo Synodontis |
| Polypterus senegalus | Cuvier'S Bichir |
| Synodontis decorus | Decorated Synodontis |
| Polypterus delhezi | Delhezi Bichir |
| Moenkhausia pitteri | Diamond Tetra |
| Hyphessobrycon amandae | Ember Tetra |
| Nematobrycon palmeri | Emperor Tetra |
| Polypterus endlicheri | Endlicheri Bichir |
| Aphyocharax alburnus | False Flame Tetra |
| Synodontis eupterus | Feathered Fin Synodontis |
| Cichlasoma festae | Festa'S Cichlid |
| Cichlasoma meeki | Firemouth Cichlid |
| Puntius pentazona | Five Banded Barb |
| Epalzeorhynchus kalopterus | Flying Fox |
| Crossocheilus siamensis | Flying Fox |
| Popondetta furcata | Forktail Rainbow |
| Cyphotilapia frontosa | Frontosa Cichlid |
| Cyathopharynx furcifer | Furcifer |
| Sturisoma fursochi | Fursochi Cat Fish |
| Aphyosemion gardneri | Gardneri Killifish |
| Pseudomugil gertrudae | Gertrudae |
| Danio malabarinchus | Giant Danio |
| Ambassis ranga | Glass Angel |
| Prionobrama filigera | Glass Bloodfin |
| Hypostomus plecostomus | Glass Cleaner Plecostomus |
| Hemigrammus rodwayi | Gold Tetra |
| Puntius sachsi | Golden Barb |
| Nannacara anomala | Golden Dwarf Cichlid |
| Nannostomus beckfordi | Golden Pencil Tetra |
| Pristella maxillaris | Golden Pristella |
| Melanotaenia herbrt axelrodi | Golden Rainbow |
| Scleropages formosus | Green Arowana |
| Brachydanio rerio | Green Danio |
| Aequidens rivulatus | Green Terror Cichlid |
| Macrognathus circumcinctus | Half Banded Spiny Eel |
| Rasbora heteromorpha | Harlequin Rasbora |
| Gasteropelecus sternicla | Hatchet Fish |
| Rasbora dorsiocellata | High Spot Rasbora |
| Geophagus steindachneri | Hondae Humphead |

TABLE 5-continued

Ornamental Fish Species

| Scientific Name | Common Name |
|---|---|
| Ctenolucius hujeta | Hujeta |
| Scleropages jardini | Jardini Arowana |
| Hemichromis paynei | Jewel Cichlid |
| Melanochromis johanni | Johanni Cichlid |
| Julidichromis dickfeldi | Juldchrmis Dickfeldi |
| Julidichromis ornatus | Julidochromis Ornatus |
| Julidichromis transcriptus | Julidochromis Transcriptus |
| Geophagus jurupari | Jurupari Cichlid |
| Tropheus IKOLA | Kaisar Tropheus |
| Hyphessobrycon loweae | Kitti Tetra |
| Stigmatogobius sadanundio | Knight Goby |
| Cyprinus Carpio | Koi |
| Acanthopthalmus kuhlii | Kuhlii Loach |
| Lamprologus silindericus | Lamprologus Silindericus |
| Lamprologus leleupi | Lemon Cichlid |
| Labidochromis caeruleus | Lemon Mbuna Cichlid |
| Hyphessobrycon pulchripinnis | Lemon Tetra |
| Ctenopoma acutirostre | Leopard Bushfish |
| Brachydanio frankei | Leopard Danio |
| Leptosoma malasa | Leptosoma Malasa |
| Rasbora paviei | Line Rasbora |
| Capoeta arulius | Long Fin Barb |
| Alesthes longipinnis | Long Fin Characin |
| Rasbora einthovenii | Long-Band Rasbora |
| Melanotaenia maccullochi | Macculloch'S Rainbow |
| Paretropheus menoramba | Madagascar Cichlid |
| Bedotia gaeyi | Madagascar Rainbow |
| Haplochromis compressiceps | Malawi Eye Biter |
| Ompok sp. | Malay Glass Catfish |
| Betta splendens | Male Betta |
| Cichlasom managuense | Managuense Cichlid |
| Polypterus palmas | Marbled Bichir |
| Xiphophorus helleri | Millenium Swordtail |
| Monodactylus argentus | Mono Angel |
| Cyrtocara moorii | Morrii |
| Sawbwa resplendens | Naked Micro Rasbora |
| Hyphessobrycon h. axelrodi sp. | Negro Brilliant Black Neon |
| Melanotaenia praecox | Neon Dwarf Rainbow |
| Aplocheillus panchax | New Golden Wonder |
| Synodontis ocellifer | Ocellated Synodontis |
| Colisa labiosa | Orange Thick Lipped Gourami |
| Polypterus ornatipinnis | Ornate Bichir |
| Botia Locahanta | Pakistani Loach |
| Puntius fasciatus | Panda Barb |
| Apistogramma pandurini | Pandurini Dwarf |
| Macropodus opercularis | Paradise Fish |
| Cichlasoma sp. | Parrot |
| Cichla Ocellaris | Peackock Bass Cichlid |
| Trichogaster leeri | Pearl Gourami |
| Cichlasoma carpinte | Pearl Scale Cichlid |
| Lamprologus calvus | Pearly Lamprologus |
| Tropheus PEMBA | Pemba River Tropheus |
| Thayeria boelkea | Penguin Tetra |
| Chalceus macrolepidotus | Pinktail Characin |
| Mogurnda mogurnda | Purple Striped Gudgeon |
| Rasbora sp. | Rasbora Red Fin |
| Aphyocharax rathbuni | Red Belly Tetra |
| Cichlasoma labiatum | Red Devil |
| Moenkhausia santaefilomenae | Red Eye Tetra |
| Pseudotrophues sp. | Red Eyed Tangarine Cichlid |
| Mastacembelus erythrotaenia | Red Fire Eel |
| Copadichromis borleyi | Red Kadango |
| Rasbora pauciperforata | Red Line Rasbora |
| Colossoma macropodum | Red Pacu |
| Megalamphodus sweglesi | Red Phantom |
| Glossolepis incisus | Red Rainbow |
| Cichlasoma severum | Red Severum Cichlid |
| Notropis lutrensis | Red Shiner |
| Megalamphodus roseus | Red Tail Yellow Phantom |
| Epalzeorhynchos frenatus | Redfin Shark |
| Epalzeorhynchos bicolor | Redtail Black Shark |
| Puntius conchonius | Rosy Barb |
| Hyphessobrycon bentosi | Rosy Tetra |
| Puntius rhombocellatus | Round Banded Clown Barb |
| Puntius nigrofasciatus | Ruby Barb |
| Hemigrammus bleheri | Rummy Nose Tetra |
| Arius graeffei | Salmon Catfish |
| Hyphessobrycon serpae | Serpae Tetra |
| Hyphessobrycon serpae sp | Serpae Tetra Veiltail |
| Osteoglossum bichirrhosum | Silver Arowana |
| Distichodus affinis | Silver Distichodus |
| Metynnis hypsauchen | Silver Dollar |
| Selenotoca multifasciata | Silver Scat |
| Hasemania nanna | Silver Tipped Tetra |
| Balantiocheilos melanopterus | Silver Tricolor Shark |
| Rasbora espei | Slender Wedge Rasbora |
| Pseudomugil signifer | Southern Blue Eye |
| Chilodus punctatus | Spotted Headstander |
| Rasbora maculata | Spotted Pygmy Rasbora |
| Metynnis maculatus | Spotted Silver Dollar |
| Puntius lineatus | Striped/Lined Barb |
| Scleropages formosus | Super Red Arowana |
| Corynopoma riseii | Swordtail Characin |
| Cichlasoma synspilum | Synspillum Cichlid |
| Iriantherina werneri | Threadfin Rainbow |
| Capoeta tetrazona | Tiger Barb |
| Pseudoplatystoma fasciatum | Tiger Shovelnose Catfish |
| Tilapia buttikoferi | Tiger Zebra Tilapia |
| Petrochromis trewavasae | Trewavas'S Petrochromis |
| Tropheus duboisi | Tropheus Duboisi |
| Mystus micracanthus | Two Spotted Catfish |
| Uaru amphiacanthoides | Uaru - Triangle Cichlid |
| Sphaerichthys vallianti | Valliant'S Gourami |
| Thayeria boehlkea sp. | Veiltail Penguin Tetra |
| Opthalmotilapia ventralis | Ventralis |
| Haplochromis venustus | Venustus |
| Synodontis schoutedeni | Vermiculated Synodntis |
| Tanichtys albonubes | White Cloud |
| Tanichtyhs albonubes | White Cloud Minnow |
| Osphronemus gourami | White Giant Gourami |
| Symphysodon aequifasciata | White Smoke |
| Aphyocharax paraguayensis | White Spot Tetra |
| Crenicichla saxalitus | White Spotted Pike Cichlid |
| Mastacembelus armatus | White Spotted Spiny Eel |
| Gymnocorymbus ternetzi | White Tetra |
| Betta coccina | Wine Red Betta |
| Melanochromis auratus | Yellow Auratus Cichlid |
| Hemmigrammopetersius caudalis | Yellow Congo |
| Apistograma borelli | Yellow Dwarf Cichlid |

The more preferred fish for use with the disclosed constructs and methods is zebrafish, *Danio rerio*. Zebrafish are increasingly popular ornamental animals and would be of added commercial value in various colors. Zebrafish embryos are easily accessible and nearly transparent. The most preferred fish for use with the disclosed constructs and methods is the Golden Zebrafish. Zebrafish skin color is determined by pigment cells in their skin, which contain pigment granules called melanosomes. The number, size and density of the melanosomes per pigment cell influence the color of the fish skin. Golden zebrafish have diminished number, size, and density of melanosomes and hence have lighter skin when compared to the wild type zebrafish. Golden zebrafish have a mutation in slc24a5 gene, slc24a5 codes for a putative cation exchanger localized to intracellular membrane, rendering the fish skin lighter or less pigmented (Lamason et al., 2005).

The disclosed transgenic fish are produced by introducing a transgenic construct into the genomes of cells of a fish, preferably embryonic cells, and most preferably in a single cell embryo. Where the transgenic construct is introduced into embryonic cells, the transgenic fish is obtained by allowing the embryonic cell or cells to develop into a fish. The disclosed transgenic constructs can be introduced into embryonic fish cells using any suitable technique. Many techniques for such introduction of exogenous genetic material have been demonstrated in fish and other animals. These include microinjection (Culp et al., (1991), electroporation (Inoue et al., 1990; Muller et al., 1993; Murakami et al., 1994; Muller et al., 1992; and Symonds et al., 1994), particle gun bombardment (Zelenin et al., 1991), and the use of liposomes (Szelei et al., 1994). The preferred method for introduction of transgenic constructs into fish embryonic cells is by microinjection.

Embryos or embryonic cells can generally be obtained by collecting eggs as soon as possible after they are laid by methods that are well known to those of ordinary experience in the ornamental fish production field. Depending on the type of fish, it is generally preferred that the eggs be fertilized prior to or at the time of collection. This is preferably accomplished by placing a male and female fish together in a tank that allows egg collection under conditions that stimulate mating. A fertilized egg cell prior to the first cell division is considered a one cell embryo, and the fertilized egg cell is thus considered an embryonic cell.

The transgene may randomly integrate into the genome of the embryo in one or more copies (concatemers). After introduction of the transgenic construct, the embryo is allowed to develop into a fish. The fish that were injected as embryos are allowed to interbreed and the offspring are screened for the presence of the transgene. Fish harboring the transgene may be identified by any suitable means. In the preferred case, one or more of the transgenic constructs will have integrated into the cellular genome, which can be probed for the presence of construct sequences. To identify transgenic fish actually expressing the transgene, the presence of an expression product can be assayed. Several techniques for such identification are known and used for transgenic animals and most can be applied to transgenic fish. Probing of potential or actual transgenic fish for nucleic acid sequences present in or characteristic of a transgenic construct can be accomplished by Southern or northern blotting, polymerase chain reaction (PCR) or other sequence-specific nucleic acid amplification techniques.

The simplest way to confirm the presence of a fluorescent protein expressing transgene in a given fish is by visual inspection, as the fish in question would be brightly colored and immediately distinguishable from non-transgenic fish. Preferred techniques for identifying fluorescent protein expressing transgenic zebrafish are described in the examples. The present invention also provides a method to obtain a new population or the progenitor of a new line of fluorescent transgenic fish exhibits strong visible fluorescence, strong visible fluorescence means that a person with 20/20 vision (i.e., average vision) will be able to distinguish between the fluorescent fish in question and a non-fluorescent fish of the same species at a distance of at least 5 feet in a lighted office, with a preferred distance of at least 10 feet in a lighted office, and a more preferred distance of at least 15 feet in a lighted office, and an even more preferred distance of at least 20 feet in a lighted office, with the illumination level defined in Table 6. One can observe all transgenic fluorescent fish from a particular population that exhibit strong visible fluorescence under the various lighting conditions and select the fish that exhibits the highest level of visible fluorescence of the fluorescent protein. Selected fish with strong visible fluorescence are monitored and selected continuously to ensure stability of expression and maintenance of the strong visible fluorescence trait. Thus a new line of fish exhibiting strong visible fluorescence is created for further breeding.

The invention further encompasses progeny of a transgenic fish containing a genomically integrated transgenic construct, as well as transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The hybrid progeny of these matings have the benefits of the transgene for fluorescence combined with the benefits derived from these other lineages.

Fertilization from Frozen Sperm

Sperm freezing methods are well known in the art, for example see Walker and Streisinger (1983). Frozen zebrafish sperm may be used to fertilize eggs also as described in Walker and Streisinger (1983), incorporated herein by references. Briefly, a droplet of ice-cold 100% Hank's saline is placed next to zebrafish eggs in a petri dish. Frozen sperm is thawed for a few seconds in air then expelled into the droplet of Hank's saline and the solution is mixed with the eggs. The mixture is incubated for about ~1 minute and then fish water added.

Vectors

The invention is further directed to a replicable vector containing cDNA that codes for the polypeptide and that is capable of expressing the polypeptide.

The present invention is also directed to a vector comprising a replicable vector and a DNA sequence corresponding to the above described gene inserted into said vector. The vector may be an integrating or non-integrating vector depending on its intended use and is conveniently a plasmid. The present invention also encompasses the removal of the vector backbone from the plasmid before the transgenic construct may be introduced into the zebrafish.

Transformed Cells

The invention further relates to a transformed cell or microorganism containing cDNA or a vector which codes for the polypeptide or a fragment or variant thereof and that is capable of expressing the polypeptide.

Expression Systems Using Vertebrate Cells

Interest has been great in vertebrate cells, and propagation of vertebrate cells in culture (tissue culture) has become a routine procedure. Examples of vertebrate host cell lines useful in the present invention preferably include cells from any of the fish described herein. Expression vectors for such cells ordinarily include (if necessary) an origin of replication, a promoter located upstream from the gene to be expressed, along with a ribosome-binding site, RNA splice site (if intron-containing genomic DNA is used or if an intron is necessary to optimize expression of a cDNA), and a polyadenylation site.

In another aspect of the present invention, also included is the commercial marketability of the transgenic fluorescent fish to the ornamental fish industry.

EXAMPLES

The invention will now be further described with reference to the following examples. These examples are intended to be merely illustrative of the invention and are not intended to limit or restrict the scope of the present invention in any way and should not be construed as providing conditions, parameters, reagents, or starting materials which must be utilized exclusively in order to practice the art of the present invention.

Example 1

Design and Generation of the Construct Plasmids

The promoter of the zebrafish fast skeletal muscle myosin light chain (zMLC2) (Ju et al., 2003) and the carp β-actin enhancer/promoter sequence (Lui et al., 1990) were cloned into pBluescript II SK (−) and pUC18 respectively. Red fluorescent protein gene, DsRed2; green fluorescent protein gene, ZsGreen1 and yellow fluorescent protein gene, ZsYellow1 were amplified by PCR from pDsRed2-N1, pZsGreen1-N1 and pZsYellow1-N1 (Clontech Inc., Matz. et al., 1999) respectively and cloned into pBluescript II SK (−) zMLC2 and pUC18-carp β-actin such that the promoter was operably linked to the fluorescent gene. Tandem SV40(A) polyA/3'UTR sequence from pK-SV40(A)X2 plasmid were cloned 3' to the fluorescent protein gene coding region. It is preferred to use more than one copy of the selected polyadenylation sequence, and more preferred to use a viral polyadenylation sequence, as this will increase the efficiency of the fluorescent protein gene expression. The resulting five construct vector maps are provided as FIG. 1 through FIG. 5.

Example 2

Preparation of the Construct for Delivery

The vectors pUC18-carp β-actin-DsRed2 and pUC18-carp β-actin-ZsGreen1 were restriction double digested with XbaI and AatII enzymes for three hours (FIG. 6, Step 1) and then run on 0.8% agarose gel to separate the transgenic insert cassette from the vector backbone (FIG. 6, Step 2 and 3). Transgenic insert cassette band (~3.5 kb) which contained the promoter, the open reading frame and the 3'UTR was excised and purified using phenol:choloroform extraction.

The transgenic vectors pBluescript II SK(−)-zMLC-DsRed2-SV40x2, pBluescript II SK(−)-zMLC-ZsGreen1-SV40x2, and pBluescript II SK(−)-zMLC-ZsYellow1-SV40x2 were restriction triple digested with XhoI, XmnI and NotI enzymes for three hours and then run on 0.8% agarose gel to separate the transgenic insert cassette from the vector backbone. The transgenic insert cassette band (~3.2 kb) which contained the promoter, the open reading frame and the 3'UTR was excised and gel purified.

Example 3

Making the Transgenic Fish

The purified transgenic insert cassette which contained the promoter, the open reading frame and the 3'UTR was microinjected into the zebrafish embryos (FIG. 6, Step 4).

While only one construct was injected into Yellow zebrafish 1, to increase the chances of developing a fish with strong visible fluorescence, more than one construct was injected simultaneously in Red zebrafish 1 and Green zebrafish 1. For the purposes of this application, strong visible fluorescence means that a person with 20/20 vision (i.e., average vision) will be able to distinguish between the fluorescent fish in question and a non-fluorescent fish of the same species at a distance of at least 5 feet in a lighted office, with a preferred distance of at least 10 feet in a lighted office, and a more preferred distance of at least 15 feet in a lighted office, and an even more preferred distance of at least 20 feet in a lighted office, with the illumination level defined in Table 6.

Given the same illumination levels, distances, and observer of average vision, another preferable quality of fish that exhibit strong visible fluorescence are those fish that also exhibit ubiquitous expression of the fluorescence, defined herein to mean strong fluorescence that is not limited to a particular tissue type or body location, with such expression preferably including fins, eyes, stripes or spots. Typically, ubiquitous fluorescent expression will mean that the fluorescent expression is visible over 75% to 100% of the body of the fish (excluding fins and eyes). The inventors have discovered that the use of a ubiquitous promoter in combination with a tissue specific promoter (such as a muscle promoter), particularly where such fish are prepared using at least two expression vectors, will generally result in fish having the desirable ubiquitous expression trait. In this more preferred example, the fluorescent pattern exhibited by the fish would also be free from any patches of non-expression or noticeably weak or dull expression, with the possible exception of non-expression in fins, eyes, and stripes or spots. Expression in the fins, eyes, and stripes or spots is also preferred, but not required for a fish to be considered as exhibiting ubiquitous fluorescent expression.

Examples of fish exhibiting strong visible fluorescence are the lines which are the subject of the present invention. Color photographs of these fish are available through World Wide Web at glofish.com/photos.asp. Color photographs of fish that are fluorescent, yet that do not exhibit strong visible fluorescence are available through World Wide Web at glofish.com/old_glofish.asp.

To obtain strong visible fluorescence, it is preferred to use a promoter that expresses ubiquitously and co-inject this promoter with a strong muscle promoter. It is also preferred to use enhancing elements in the transgenic insert cassette. For example, in the present invention, both Red zebrafish 1 and Green zebrafish 1 incorporate more than one transgenic expression cassette, with one being a ubiquitous promoter, and the other being a strong muscle promoter. In particular, Red zebrafish 1 incorporates the cassettes represented by FIG. 1 and FIG. 4, and Green zebrafish 1 incorporates the cassettes represented by FIG. 2 and FIG. 5. In the cassette that includes the ubiquitous promoter, there is also an intron and exon, which exemplifies the type of RNA processing element that is helpful in achieving strong visible fluorescence.

To co-inject the embryos, multiple purified transgenic insert cassettes can simply be loaded into the microinjection needle simultaneously and then injected. Alternatively, in the preferred method, the injection of constructs containing multiple (two or more) fluorescent protein expression cassettes can be made using common molecular biology techniques, such as DNA digestion and ligation. In the most preferred method, a plasmid can be made which contains several fluorescent protein expression cassettes in tandem, and then treated in the same way as disclosed herein for a single fluorescent protein expressing plasmid (that is, made, isolated, purified, and linearized with the antibiotic resistance marker gene and replication origin removed before injection). While the present invention incorporates only the transgenic insert cassettes shown in the Figures, it is understood that multiple transgenic insert cassettes of any type can be simultaneously injected into a fish embryo from any species. Once injected, the embryos were allowed to grow into adult fish. At that point, they were spawned to determine if their offspring carried the fluorescence trait. The preferred method of spawning is a single pair spawn between a zebrafish that had been injected as an embryo and a wild-type zebrafish. The offspring of the transgenic zebrafish were raised to maturity and the fluorescent fish selected for further examination. In the preferred method, the offspring should be screened for by exposure to lights of specific wavelengths while they are still embryos. For example, for green fluorescent protein an excitation max at 493 nm with emission max at 505 nm, for red fluorescent protein an excitation max at 563 nm and an emission max at 582 nm and for yellow fluorescent protein an excitation max at 529 nm and an emission max at 539 nm was used corresponding, for example, to ZsGreen1, DsRed2 and ZsYellow1.

The foregoing method was used to screen for the most esthetically pleasing fish while still maintaining the ability to efficiently breed.

Example 4

Selecting the Transgenic Fish

Any fish showing fluorescence as embryos or juveniles were grown to maturity and examined for fluorescence as an adult to determine which specific fluorescent fish was to be used as a progenitor for a new line. In this endeavor, the most valuable expression pattern is one that meets the definition of a fish exhibiting strong visible expression as defined herein, and even more preferred are those that also exhibit ubiquitous expression, as this strong expression would increase both the aesthetic appeal and commercial value of the fish. In particular, it is important to be sure the fish exhibits strong visible fluorescence in all of the lighting conditions described in Table 6 below.

TABLE 6

Common Light Levels - Indoors and Outdoors

| Condition | Illumination (lux) |
| --- | --- |
| Full Daylight | 10,000 |
| Overcast Day | 1000 |
| Lighted Home | >150 |
| Lighted Office | 500 |
| Dark Indoor Room | <50 |
| Moderately Lit Room | 100-150 |

Accordingly, to ensure that a progenitor for a new line of fluorescent fish exhibits strong visible fluorescence, one can observe all transgenic fluorescent fish from a particular population that exhibit strong visible fluorescence under the various lighting conditions noted above in Table 6, and select the fish that exhibits the highest level of visible fluorescence of the fluorescent protein. Selection of this fish is based on visible observation only, as commercial appeal will be based on visual appearance. When testing the fish in a completely dark room, it is preferred to use an ultraviolet light to observe the level of the fish's fluorescent expression, as the ambient light will typically be insufficient to observe even the most strongly expressing fluorescent fish.

It is also preferred to provide fish that exhibit a reasonably stable color over the entire life of the fish, varying no more than about 20% at any given age as compared to very young fish of the same line. For example, the inventors have noted that some fish, particularly those that are not prepared by the more preferred methods of the present invention, tend to dramatically lose their color brilliance over time, and can become indistinguishable from non-transgenic fish of the same species, even as young as one year old. Preferred transgenic fish of the present invention can be selected for this trait by monitoring the fish over its development cycle. It is also preferred to select fish that are stable without regard to the ambient physical environment of the tank (e.g., color of gravel, plants, etc.). This can be ensured by selecting fish that do no lose their color brilliancy over time or in response to the physical environment.

Mendelian inheritance of the fluorescent trait is consistent with an integration event at a single locus in the selected fish. The progeny from the originally selected zebrafish comprising this particular transgenic event can be used for further breeding through traditional means with unmodified zebrafish to establish a new line of fluorescent fish through methods that are well known to those of ordinary skill in the production of fish, wherein the vast majority of fluorescent fish derived from this progenitor exhibited a materially similar fluorescence pattern and strength as the founding fish. It is also preferred that the selected fish be monitored for stability and consistency of expression, as any life-cycle variance from strong visible fluorescence that is seen in the selected fish may be passed along to the offspring. Additionally, to facilitate consistency of expression, it is also necessary to remove from the breeding population of this line any fish that appear from time to time with an expression pattern which is visibly weaker than the original founder.

The specific transgenic events embodied in these fish are designated Red zebrafish 1, Green zebrafish 1 and Yellow zebrafish 1 respectively. Sperm from these fish may be used to fertilize zebrafish eggs and thereby breed transgenic zebrafish that comprise these specific transgenic integration events. Sperm from each line is deposited at the European Collection of Cell Cultures (ECACC) as "Red zebrafish 1" (provisional accession no. 06090403), "Green zebrafish 1" (provisional accession no. 06090401) and "Yellow zebrafish 1" (provisional accession no. 06090402).

Example 6

Breeding the Transgenic Fish

Once the transgenic line had been established as described above, fish that were homozygous for the fluorescence trait were obtained by crossing fish that were heterozygous for the fluorescence trait, and then the progeny were screened to determine whether they were homozygous for the fluorescence trait. The preferred method of screening the progeny is through a test cross with a wild-type zebrafish, where any fluorescent fish that produces 100% fluorescent offspring would be homozygous for the fluorescent trait. Once enough homozygous fish were found to create a minimal breeding population, they were crossed to produce additional homozygous progeny. Upon adulthood, these progeny were crossed with wild-type fish to obtain progeny that were heterozygous for the fluorescent trait. These heterozygous fish were then sold to the commercial ornamental fish market, while the homozygous fish population was maintained through traditional methods to ensure a future homozygous breeding population.

Example 7

Potential Application of the Transgenic Fish

The fluorescent transgenic fish have use as ornamental fish in the market. Stably expressing transgenic lines can be developed by breeding a transgenic individual with a wild type fish, mutant fish or another transgenic fish. Multiple color fluorescent fish may be generated by the same technique as red fluorescent fish, yellow fluorescent fish and green fluorescent fish. By recombining different tissue specific promoters and fluorescent protein genes, more varieties of transgenic fish of different fluorescent color patterns will be created. By expression of two or more different fluorescent proteins in the same tissue, an intermediate color may be created. For example, combing expression of both red fluorescent protein gene and yellow fluorescent protein gene under a muscle-specific promoter, an orange fluorescent zebrafish may be created.

The fluorescent transgenic fish should also be valuable in the market for scientific research tools because they can be used for embryonic studies such as tracing cell lineage and cell migration. Cells from transgenic fish expressing green fluorescent protein can also be used as cellular and genetic markers in cell transplantation and nuclear transplantation experiments. Additionally these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pub No. US 2004/0143864
Barolo et al., *Biotechniques*, 36(3):436-440; 442, 2004.
Bourett et al., *Fungal Genet. Biol.*, 37(3):211-220, 2002.
Brem et al., *Aquaculture*, 68:209-219, 1988.
Carvan et al., *Ann. NY Acad. Sci.*, 919:133-147, 2000.
Chen et al., *J. Virol.*, 62:3883-3887, 1988.
Cho et al., *Insect. Biochem. Mol. Biol.*, 36(4):273-281, 2006.
Chourrout et al., *Aquaculture*, 51:143-150, 1986.
Clark et al., *Phil. Trans. R. Soc. Lond. B.*, 339:225-232, 1993.
Cozzi and White, *Nat. Med.*, 1(9):964-966, 1995.
Culp et al., *Proc. Natl. Acad. Sci. USA*, 88(18):7953-7957, 1991.
Delvin et al., *Can. J. Fisheries Aqua. Sci.*, 52:1376-1384, 1995.
Delvin et al., *Nature*, 371:209-210, 1994.
Du et al., *Bio/Technology*, 10:176-181, 1992.
Eckert et al., *FEMS Microbiol. Lett.*, 253(1):67-74, 2005.
Finley et al., *Biotechniques*, 31(1):66-70; 72, 2001.
Gong et al., *Biochem. Biophys. Res. Commun.*, 308(1):58-63, 2003.
Gordon et al., *Proc. Natl. Acad. Sci. USA*, 77:7380-7384, 1980.
Gross et al., *Aquaculature*, 103:253-273, 1992.
Hadjantonakis et al., *Nat. Rev. Genet.*, 4(8):613-625, 2003.
Hamada et al., *Brain Res. Mol. Brain Res.*, 139(1):42-51, 2005.
Handler and Harrell, *Biotechniques*, 31(4):820; 824-828, 2001.
Horn et al., *Insect. Biochem. Mol. Biol.*, 32(10):1221-1235, 2002.
Inoue et al., *Cell. Differ. Develop.*, 29:123-128, 1990.
Ju et al., *Dev Dyn.*, 227(1):14-26, 2003.
Khoo et al., *Aquaculture*, 107:1-19, 1992.
Kollias and Grosveld, In: *The Study of Gene Regulation in Transgenic Mice*, Transgenic Animals, Grosveld and Kollias (Eds.), Academic Press, 79-98, 1992.
Lamason et al., *Science*, 310(5755):1782-1786, 2005.
Lathe and Mullins, *Transgenic Res.*, 2(5):286-299, 1993.
Liu et al., *Biotechnology*, 8:1268-1272, 1990.
Long et al., *BMC Biotechnol.*, 5:20, 2005.
Maga and Murray, *Biotechnology*, 13(13):1452-1457, 1995.
Matz et al., *Nat. Biotechnol.*, 17:969-973, 1999.
Mikkelsen et al., *FEMS Microbiol. Lett.*, 223(1):135-139, 2003.
Miyawaki, *Cell Struct. Funct.*, 27(5):343-347, 2002.
Muller et al., *FEBS Lett.*, 324:27-32, 1993.
Muller et al., *Mol. Mar. Biol. Biotechnol.*, 1:276-281, 1992.
Murakami et al., *J. Biotechnol.*, 34:35-42, 1994.
Navarro et al., *J. Virol.*, 78(9):4744-4752, 2004.
Palmiter et al., *Nature*, 300:611-615, 1982.
Palmiter et al., *Proc. Natl. Acad. Sci. USA*, 88:478-482, 1991.
Penman et al., *Aquaculture*, 85:35-50, 1990.
Powers et al., *Mol. Marine Biol. Biotechnol.*, 1:301-308, 1992.
Royer et al., *Transfenic Res.*, 14(4):463-472, 2005.
Sambrook and Russell, Molecular Cloning: A Laboratory Manual $3^{rd}$ Ed., Cold Spring Harbor Laboratory Press, 2001.
Sambrook et al., In: *Molecular cloning: a laboratory manual*, $2^{nd}$ Ed., Cold Spring Harbor Laboratory Press, Cold Spring Harbor, N.Y., 1989.
Sarkar et al., *BMC Biotechnol.*, 6(1):27, 2006.
Sato et al., *Biochem. Biophys. Res. Commun.*, 311(2):478-481, 2003.
Schmid et al., *Glia*, 53(4):345-351, 2006.
Sin et al., *Aquaculature*, 117:57-69, 1993.
Sippel et al., In: *The Regulatory Domain Organization of Eukaryotic Genomes: Implications For Stable Gene Transfer*, Transgenic Animals, Grosveld and Kollias (Eds.), Academic Press, 1-26, 1992.
Symonds et al., *Aquaculture*, 119:313-327, 1994.
Szelei et al., *Transgenic Res.*, 3:116-119, 1994.
Tolar et al., *Mol. Ther.*, 12(1):42-48, 2005.
Tsai et al., *Can. J. Fish Aquat. Sci.*, 52:776-787, 1995.
Vintersten et al., *Genesis*, 40(4):241-246, 2004.
Walker and Streisinger, *Genetics* 103: 125-136, 1983.
Wall et al., *Nat. Struct. Biol.*, 7(12):1133-1138, 2000.
Wenck et al., *Plant Cell Rep.*, 22(4):244-251, 2003.
Werdien et al., *Nucleic Acids Res.*, 29(11):E53-3, 2001.
Wouters et al., *Physiol. Genomics*, 2(3):412-421, 2005.
Wright et al., *Biotechnology*, 9:830-834, 1991.
Xu et al., *DNA Cell Biol.*, 18, 85-95, 1999.
Zelenin et al., *FEBS Lett.*, 287(1-2):118-120, 1991.
Zeller et al., *Dev. Dyn.*, 235(2):456-467, 2006.
Zhu and Zon, *Methods Cell Biol.*, 76:3-12, 2004.
Zhu et al., *Dev. Biol.*, 281(2):256-269, 2005.
Zhu et al., *Z. Angew. Ichthyol.*, 1:31-34, 1985.

What is claimed is:

1. A transgenic fluorescent fish comprising in its genome:
   (a) a first transgene encoding a first fluorescent protein, wherein said first transgene is under the control of a ubiquitous promoter, and
   (b) a second transgene encoding a second fluorescent protein, wherein said second transgene is under the control of a tissue specific promoter;
   wherein said transgenic fluorescent fish exhibit a strong visible fluorescence over 75% to 100% of the body of said fish, optionally excluding fins and eyes; and
   wherein said first and second transgenes are both chromosomally integrated at the same, single locus.

2. The transgenic fish of claim 1, wherein the first and second fluorescent proteins are ZsGreen1, ZsYellow1, DsRed2, GFP, eGFP, YFP, eYFP, BFP, eBFP, CFP, eCFP, FP, AmCyan1, DsRed-Express, AsRed2, HcRed1, mPlum, mCherry, tdTomato, mStrawberry, J-Red, DsRed-monomer, mOrange, mKO, MCitrine, Venus, Ypet, EYFP, Emerald, CyPet, mCFPm, Cerulean, or T-Sapphire.

3. The transgenic fish of claim 2, wherein the first and second fluorescent proteins are ZsGreen1.

4. The transgenic fish of claim 2, wherein the first and second fluorescent proteins are DsRed 2.

5. The transgenic fish of claim 1, wherein said fish β-actin promoter is a carp β-actin promoter.

6. The transgenic fish of claim 1, wherein said fish myosin light chain promoter is a zebrafish fast skeletal myosin light chain promoter.

7. The transgenic fluorescent fish of claim 1, wherein each of said genes comprise at least two polyadenylation signals positioned in tandem.

8. The transgenic fluorescent fish of claim 7, wherein said polyadenylation signals are viral polyadenylation signals.

9. The transgenic fluorescent fish of claim 8, wherein said viral polyadenylation signals are SV40 polyadenylation sequences.

10. The transgenic fluorescent fish of claim 1, wherein said muscle specific promoter is a fish myosin light chain promoter.

11. The transgenic fluorescent fish of claim 1, wherein said ubiquitous promoter is a fish β-actin promoter.

12. The transgenic, fluorescent fish of claim 1, wherein the transgenic, fluorescent fish is further defined as a transgenic, fluorescent zebrafish, catfish, zebrafish, medaka, carp, tilapia, goldfish, tetras, barbs, sharks of the family cyprinidae, angelfish, loach, koi, glassfish, catfish, angel fish, discus, eel, tetra, goby, gourami, guppy, Xiphophorus, hatchet fish, Molly fish, or pangasius.

13. The transgenic, fluorescent fish of claim 12, wherein the transgenic, fluorescent fish is further defined as a transgenic, fluorescent zebrafish, tetra or barb.

14. The transgenic fish of claim 13, wherein the transgenic, fluorescent fish is a transgenic zebrafish.

15. The transgenic zebrafish of claim 14, wherein the transgenic zebrafish is a fertile, transgenic zebrafish.

16. The transgenic zebrafish of claim 14, wherein the transgenic zebrafish is a transgenic golden zebrafish.

17. The transgenic zebrafish of claim 1, wherein the first and second transgene encode the same fluorescent protein.

18. The transgenic zebrafish of claim 1, wherein the tissue specific promoter is further defined as a muscle specific promoter.

* * * * *

SEQUENCE LISTING

<160> NUMBER OF SEQ ID NOS: 5

<210> SEQ ID NO 1
<211> LENGTH: 3119
<212> TYPE: DNA
<213> ORGANISM: Artificial
<220> FEATURE:
<223> OTHER INFORMATION: Cloned expression cassette

<400> SEQUENCE: 1

| | | | | | |
|---|---|---|---|---|---|
| ggccgcaaca | gcggaatgac | cacatttgta | gaggttttac | ttgctttaaa | aaacctccca | 60 |
| catctccccc | tgaacctgaa | acataaaatg | aatgcaattg | ttgttgttaa | cttgtttatt | 120 |
| gcagcttata | atggttacaa | ataaagcaat | agcatcacaa | atttcacaaa | taaagcattt | 180 |
| ttttcactgc | attctagttg | tggtttgtcc | aaactcatca | atgaccacat | ttgtagaggt | 240 |
| tttacttgct | ttaaaaaacc | tcccacatct | ccccctgaac | ctgaaacata | aaatgaatgc | 300 |
| aattgttgtt | gttaacttgt | ttattgcagc | ttataatggt | tacaaataaa | gcaatagcat | 360 |
| cacaaatttc | acaaataaag | cattttttc | actgcattct | agttgtggtt | tgtccaaact | 420 |
| catcaatgaa | ctctggatca | ctagtctaca | ggaacaggtg | gtggcggccc | tcggtgcgct | 480 |
| cgtactgctc | cacgatggtg | tagtcctcgt | tgtgggaggt | gatgtccagc | ttggcgtcca | 540 |
| cgtagtagta | gccgggcagc | tgcacgggct | tcttggccat | gtagatagac | ttgaactcca | 600 |
| ccaggtagtg | gccgccgtcc | ttcagcttca | gggccttgtg | ggtctcgccc | ttcagcacgc | 660 |
| cgtcgcgggg | gtacaggcgc | tcggtggagg | cctcccagcc | catggtcttc | ttctgcatca | 720 |
| cggggccgtc | ggaggggaag | ttcacgccga | tgaacttcac | cttgtagatg | aagcagccgt | 780 |
| cctgcaggga | ggagtcctgg | gtcacggtcg | ccacgccgcc | gtcctcgaag | ttcatcacgc | 840 |
| gctcccactt | gaagccctcg | gggaaggaca | gcttcttgta | gtcggggatg | tcggcgggt | 900 |
| gcttcacgta | caccttggag | ccgtactgga | actgggggga | caggatgtcc | caggcgaagg | 960 |
| gcaggggcc | gcccttggtc | accttcagct | tcacggtgtt | gtggccctcg | tagggcggc | 1020 |
| cctcgccctc | gccctcgatc | tcgaactcgt | ggccgttcac | ggtgccctcc | atgcgcacct | 1080 |
| tgaagcgcat | gaactcggtg | atgacgttct | cggaggaggc | catgaattcg | tgtgaagtct | 1140 |
| aagaagatca | agaagagaag | tctgaagccg | cgtagtgtcc | tgtacttgag | ggcttatat | 1200 |
| actgacgaag | gccccttgct | aattatagac | ccaaccttaa | gtgaggtttg | ggaaatagca | 1260 |
| gaccgagaga | gaaagaggaa | aaactatgag | gtaggggaa | agtgatggag | ggacaccggc | 1320 |
| tgggatgtac | tatcatctta | cagtgctcag | aaatagctat | tggagtcttg | aatgggatg | 1380 |
| aatctgatac | tgatggcagc | ggcctgcatg | tctcgcgttg | tctaataagg | acatggggac | 1440 |
| gtaagggact | gtttgagctt | catacaatca | cataactcaa | tttgaaatga | atgagctgta | 1500 |
| gccactgagt | ctaaagggga | cgcaactccc | tcccctaaag | ttagattagc | agcagatcaa | 1560 |
| tactggctta | tcttgcagga | ttacttgttg | gatggggagg | gttgcagtga | tagatcctga | 1620 |
| tggatttcaa | tccagagatt | tttgagccaa | tgattatgtt | gttcatatt | gttcacgccc | 1680 |
| tggctgatat | ataagaggac | gttctggtgt | cttaacccctt | atttcaaatc | agccctaatc | 1740 |
| gaaaataggt | tttaatgctt | ttcctagtat | agtgatgctg | taagatttcg | gttcaagtgc | 1800 |
| ccccaccaca | cccgtccaca | tggccatgcc | catattcagc | actctctctc | tctctctctc | 1860 |
| tctctctctc | tgccgatcga | cctatgacct | cacccggtca | cttcagtgac | tgtgaggtgc | 1920 |
| catttgtggg | aagctgccct | gtggacaagc | acgtaattac | ccctttttcc | cagttttag | 1980 |
| atggtcagca | cactacagcc | ctctgagtgg | ttgatgttgg | accctcatga | agagaaattt | 2040 |

-continued

```
gaggcttaag acagttttt tttgggaagg caggcataag gaacagctgt ggtgaccaaa     2100
atagctaaac aatcttgagc gctccttgct ctcttttct tgtctaattc atcagtcact     2160
gttttgcccc ccttgagttt gttgtgcatt cccttctttc tttagactaa tttgatatcc    2220
tgtgagtctg tcggcttgtt ttgctcctgc ttgttccaaa attgtttaag attagcatta    2280
ttttacagta cctagaaaaa cagataatta cagtgcttag agtaattgag tacagcccat    2340
tttgaaaatg aatattttc tccatctctc agtgaatata ggcaatgtat tttggtgcat    2400
ttaaacaaaa cagatttatt aaacagctat atttattaaa ataatatttt agtcacaaaa    2460
ttgaaagata aaacaattta aataaagcta aatattgcaa caaaaaatt acaacctaca    2520 aattttgaac taatttttt ccattgtttt gcttctcttg attttcccct gtttataaat     2580
ttgtatttaa tattttcaa taacatataa atatgggtgt agtagttttt ggaccgttat     2640
cataagttat tttgttaaat aagctccaga tttagcttca ctctcagaaa taaagggcgt    2700
gagctgtcac tggggtggta ccttccaaa tgataaaaat ttgtacctta aaggtccata    2760
ataaaacctc aagggtatat attagtacct aaaagtaca aaagtgtttc tcttaaaatt    2820
tttaggcact aatatatact tttgagggtat caatatggac cctttaagta caaatatgta    2880
ccttttgaaa aggtaccacc gcagtgacag cttgcggacc atttatttct gagagtgtac    2940
tgactaatct aatgtatatg cacaaatata acatagcttc ctattaaaaa tattaattta    3000
aaagacagat ttgggtgttt cccagtgtag ggttgcaact ggatgggcat ccgctgcata    3060 aaaatacac tggatgagtt ggtggctcat tcctctgtgg cgatcgatac cgtcgacct      3119
```

<210> SEQ ID NO 2
<211> LENGTH: 3656
<212> TYPE: DNA
<213> ORGANISM: Artificial
<220> FEATURE:
<223> OTHER INFORMATION: Cloned expression cassette

<400> SEQUENCE: 2

```
ctagaaccat gattacgcca agcttttaga ccttcttact tttggggatt atataagtat      60
tttctcaata aatatctcat atcttactgt ggtttaactg ctgaatctaa aattttaata    120
caaaagtagt tatatttgtt gtacattgta aactataact taacttcagt ttcagagaaa    180
ctcatgtgct caaatgtaa aaaagtttc ctgttaaata ttttgtaaat gtattgaaga    240
caaaataaga aaaaaaaaa tataagccac taaatcacac tgtccttggt atcagcaaga    300
gattctgaca taatcagctg ttttttgttta ttactgccat tgaaggccat gtgcattagt    360
cccaagttac acattaaaaa gtcacatgta gcttaccaac atcagtgctg ttcaagcaca    420
gcctcatcta ctattcaaac tgtggcacca tctaaaatat gccagaattt ttttatttaa    480
tgaatttgac cctgaaatat gtattaatat cactcctgtg atttttttgt aatcagctta    540
caattacagg aatgcaagcc tgattcatta caagtttcac tacactttct ctgacaacat    600
cacctactga actcagacca gctagttgct ccttaagtat acaatcatgt cactaatcct    660
catttcaatg aaaatacccc ctattgtact tggtacttgg tagataacca cagagcagta    720
ttatgccatt attgtgaata caataagagg taaatgacct acagagctgc tgctgctgtt    780
gtgttagatt gtaaacacag cacaggatca aggaggtgtc catcactatg accaatacta    840
gcactttgca caggctcttt gaaaggctga aagagccttt attggcgtta tcacaacaaa    900
atacgcaaat acgaaaaca acgtattgaa cttcgcaaac aaaaaacagc gattttgatg    960
```

-continued

```
aaaatcgctt aggccttgct cttcaaacaa tccagcttct ccttctttca ctctcaagtt    1020
gcaagaagca agtgtagcaa tgtgcacgcg acagccgggt gtgtgacgct ggaccaatca    1080
gagcgcagag ctccgaaagt ttaccttta tggctagagc cggcatctgc cgtcatataa     1140
aagagcgcgc ccagcgtctc agcctcactt tgagctcctc cacacgcagc tagtgcggaa    1200
tatcatctgc ctgtaaccca ttctctaaag tcgacaaacc cccccaaacc taaggtgagt    1260
tgatctttaa gctttttaca ttttcagctc gcatatatca attcgaacgt ttaattagaa    1320
tgtttaaata aagctagatt aaatgattag gctcagttac cggtcttttt tttctcattt    1380
acgtgcgaac tctgcttaaa ctctagttat tctttattaa tatgtggtta tttttatata    1440
tgtatgttat cataactgta ctggctatgt caggtggtaa tgactgtaac gttacgttac    1500
tcgttgtagg cacgacattg aatgggccgg tgttgaaata agtcttcaac ccctttaac    1560 ctcaaaatgt gctctggtta acaaggattt taacagctat cagtatgact gtgcggtttt    1620
aaagccgtta gtgaggcacg ttgcacactt gatggatggc cggaatggga agttctttat    1680
gcaggcagtg ctgcagcagg gtgtgaccta ctttagctaa cgttagccgg ctaaccagca    1740
ttcatctgcc ggtaacttga gtctaatatt ctctatgtga tatcgaagtg atcaaagaca    1800
cgtctgttag ctcactttaa ccaactgtag tgaaaaatag cgcagtgtgc agcccttcaa    1860
gtctttcatt taggctgatt attcaatcat tttattaact attaacgcgt tactaaacgt    1920
aaggtaacgt agtcagtttt taataactgg tgaaagtac tggttgggtt taaatggtga    1980
cttataattg tgttggaggg ggaaaccttt ttgataaagg ctatataatc tcaaatgaat    2040
gggctgagga tggtgttcac aggtgcttta gtgaagtccg ctcgtgaaga gtcgctgaag    2100
tgactgcaga tctgtagcgc atgcgttttg gcagacggcc gttgaaattc ggttgagtaa    2160
ttgataccag gtgaggctag aggatgtaga aattcatttg tgtagaattt agggagtggc    2220
ctggcgtgat gaatgtcgaa atccgttcct ttttactgaa ccctatgtct ctgctgagtg    2280
ccacaccgcc ggcacaaagc gtctcaaacc attgcctttt atggtaataa tgagaatgca    2340
gagggacttc ctttgtctgg cacatctgag gcgcgcattg tcacactagc acccactagc    2400
ggtcagactc agacaaaaca ggaagctgac tccacatggt cacatgctca ctgaagtgtt    2460
gacttccctg acagctgtgc actttctaaa ccggttttct cattcattta cagttcagcc    2520
gggtaccgaa ttcatggcct cctccgagaa cgtcatcacc gagttcatgc gcttcaaggt    2580
gcgcatggag ggcaccgtga acggccacga gttcgagatc gagggcgagg gcgagggccg    2640
cccctacgag ggcacaaaca ccgtgaagct gaaggtgacc aagggcggcc ccctgccctt    2700
cgcctgggac atcctgtccc cccagttcca gtacggctcc aaggtgtacg tgaagcaccc    2760
cgccgacatc cccgactaca agaagctgtc cttccccgag ggcttcaagt gggagcgcgt    2820
gatgaacttc gaggacggcg gcgtggcgac cgtgacccag gactcctccc tgcaggacgg    2880
ctgcttcatc tacaaggtga agttcatcgg cgtgaacttc cctccgacg gccccgtgat    2940 gcagaagaag accatgggct gggaggcctc caccgagcgc ctgtaccccc gcgacggcgt    3000
gctgaagggc gagacccaca aggccctgaa gctgaaggac ggcggccact acctggtgga    3060
gttcaagtct atctacatgg ccaagaagcc cgtgcagctg cccggctact actacgtgga    3120
cgccaagctg gacatcacct cccacaacga ggactacacc atcgtggagc agtacgagcg    3180
caccgagggc cgccaccacc tgttcctgta gactagtgat ccagagttca ttgatgagtt    3240
tggacaaacc acaactagaa tgcagtgaaa aaaatgcttt atttgtgaaa tttgtgatgc    3300
tattgcttta tttgtaacca ttataagctg caataaacaa gttaacaaca acaattgcat    3360
```

```
tcattttatg tttcaggttc aggggagat gtgggaggtt ttttaaagca agtaaaacct    3420
ctacaaatgt ggtcattgat gagtttggac aaaccacaac tagaatgcag tgaaaaaaat    3480
gctttatttg tgaaatttgt gatgctattg ctttatttgt aaccattata agctgcaata    3540
aacaagttaa caacaacaat tgcattcatt ttatgtttca ggttcagggg gagatgtggg    3600
aggtttttta aagcaagtaa aacctctaca atgtggtca ttccgctgtt gacgtc        3656

<210> SEQ ID NO 3
<211> LENGTH: 3151
<212> TYPE: DNA
<213> ORGANISM: Artificial
<220> FEATURE:
<223> OTHER INFORMATION: Cloned expression cassette

<400> SEQUENCE: 3
ggccgcaaca gcggaatgac cacatttgta gaggttttac ttgctttaaa aaacctccca      60
catctccccc tgaacctgaa acataaaatg aatgcaattg ttgttgttaa cttgtttatt     120
gcagcttata atggttacaa ataaagcaat agcatcacaa atttcacaaa taaagcattt     180
ttttcactgc attctagttg tggttttgtcc aaactcatca atgaccacat tgtagaggt    240 tttacttgct ttaaaaaacc tcccacatct cccctgaac ctgaaacata aatgaatgc      300 aattgttgtt gttaacttgt ttattgcagc ttataatggt tacaaataaa gcaatagcat    360
cacaaatttc acaaataaag cattttttc actgcattct agttgtggtt tgtccaaact    420
catcaatgaa ctctggatca ctagtctcag ggcaaggcgg agccggaggc gatggcgtgc    480
tcggtcaggt gccacttctg gttcttggcg tcgctgcggt cctcgcgggt cagcttgtgc    540
tggatgaagt gccagtcggg catcttgcgg ggcacggact tggccttgta cacggtgtcg    600
aactggcagc gcaagcggcc accgtccttc agcagcaggt acatgctcac gtcgcccttc    660
aagatgccct gcttgggcac ggggatgatc ttctcgcagg agggctccca gttgtcggtc    720
atcttcttca tcacggggcc gtcggcgggg aagttcacgc cgtagaactt ggactcgtgg    780
tacatgcagt tctcctccac gctcacggtg atgtcggcgt tgcagatgca cacggcgccg    840
tcctcgaaca ggaaggagcg gtcccaggtg tagccggcgg ggcaggagtt cttgaagtag    900
tcgacgatgt cctgggggta ctcggtgaac acgcggttgc cgtacatgaa ggcggcggac    960
aagatgtcct cggcgaaggg caaggggccg ccctccacca cgcacaggtt gatggcctgc   1020
ttgcccttga aggggtagcc gatgccctcg ccggtgatca cgaacttgtg gccgtccacg   1080 cagcccctcca tgcggtactt catggtcatc tccttggtca ggccgtgctt ggactgggcc   1140
atggtggcga ccgtcgaatt cgtgtgaagt ctaagaagat caagaagaga agtctgaagc   1200
cgcgtagtgt cctgtacttg aggggcttat atactgacga aggccccttg ctaattatag   1260
acccaacctt aagtgaggtt tgggaaatag cagaccgaga gagaagagg aaaaactatg    1320 aggtaggggg aaagtgatgg agggacaccg gctgggatgt actatcatct tacagtgctc   1380
agaaatagct attggagtct tggaatggga tgaatctgat actgatggca gcggcctgca   1440
tgtctcgcgt tgtctaataa ggacatgggg acgtaaggga ctgtttgagc ttcatacaat   1500
cacataactc aatttgaaat gaatgagctg tagccactga gtctaaaggg gacgcaactc   1560 cctccccctaa agttagatta gcagcagatc aatactggct tatcttgcag gattacttgt   1620
tggatgggga gggttgcagt gatagatcct gatggatttc aatccagaga ttttttgagcc   1680 aatgattatg ttgttcatat ttgttcacgc cctggctgat atataagagg acgttctggt   1740
```

```
gtcttaaccc ttatttcaaa tcagccctaa tcgaaaatag gttttaatgc tttcctagt    1800
atagtgatgc tgtaagattt cggttcaagt gcccccacca cacccgtcca catggccatg   1860
cccatattca gcactctctc tctctctctc tctctctctc tctgccgatc gacctatgac   1920
ctcacccggt cacttcagtg actgtgaggt gccatttgtg ggaagctgcc ctgtggacaa   1980
gcacgtaatt accccttttt cccagttttt agatggtcag cacactacag ccctctgagt   2040
ggttgatgtt ggaccctcat gaagagaaat tgaggctta agacagtttt tttttgggaa    2100
ggcaggcata aggaacagct gtggtgacca aaatagctaa acaatcttga gcgctccttg   2160
ctctcttttt cttgtctaat tcatcagtca ctgttttgcc cccttgagt tgttgtgca     2220
ttcccttctt tctttagact aatttgatat cctgtgagtc tgtcggcttg ttttgctcct   2280
gcttgttcca aaattgttta agattagcat tattttacag tacctagaaa acagataat    2340
tacagtgctt agagtaattg agtacagccc attttgaaaa tgaatatttt tctccatctc   2400
tcagtgaata taggcaatgt attttggtgc atttaaacaa aacagattta ttaaacagct   2460
atatttatta aaataatatt ttagtcacaa aattgaaaga taaaacaatt taaataaagc   2520
taaatattgc aacaaaaaaa ttacaaccta caaattttga actaatttt ttccattgtt    2580
ttgcttctct tgattttccc ctgttttataa atttgtattt aatattttc aataacatat   2640
aaatatgggt gtagtagttt ttggaccgtt atcataagtt attttgttaa ataagctcca   2700
gatttagctt cactctcaga aataaagggc gtgagctgtc actggggtgg taccttttcca  2760
aatgataaaa atttgtacct taaaggtcca taataaaacc tcaagggtat atattagtac   2820
ctaaaaagta caaagtgtt tctcttaaaa ttttaggca ctaatatata cttttgaggt    2880
atcaatatgg acccttaag tacaaatatg tacctttga aaggtacca ccgcagtgac     2940
agcttgcgga ccatttattt ctgagagtgt actgactaat ctaatgtata tgcacaaata   3000
taacatagct tcctattaaa aatattaatt taaaagacag atttgggtgt ttcccagtgt   3060
agggttgcaa ctggatgggc atccgctgca taaaaaatac actggatgag ttggtggctc   3120
attcctctgt ggcgatcgat accgtcgacc t                                  3151
```

<210> SEQ ID NO 4
<211> LENGTH: 3153
<212> TYPE: DNA
<213> ORGANISM: Artificial
<220> FEATURE:
<223> OTHER INFORMATION: Cloned expression cassette

<400> SEQUENCE: 4

```
ggccgcaaca gcggaatgac cacatttgta gaggttttac ttgctttaaa aaacctccca    60
catctccccc tgaacctgaa acataaaatg aatgcaattg ttgttgttaa cttgtttatt   120
gcagcttata atggttacaa ataaagcaat agcatcacaa atttcacaaa taagcatt     180
ttttcactgc attctagttg tggtttgtcc aaactcatca atgaccacat tgtagaggt    240
tttacttgct ttaaaaaacc tcccacatct cccctgaac ctgaaacata aaatgaatgc    300
aattgttgtt gttaacttgt ttattgcagc ttataatggt tacaaataaa gcaatagcat   360
cacaaatttc acaaataaag cattttttc actgcattct agttgtggtt tgtccaaact   420
catcaatgaa ctctggatca ctagtgcttc aggccagggc gctggggaag gcgatggcgt   480
gctcggtcag ctgccacttc tggttcttgg cgtcgctccg gtcctccgc agcagcttgt   540
gctgatgaa gtgccactcg gcatcttgc tgggcacgct cttggccttg tacacggtgt   600
cgaactggca ccggtaccgg ccgccgtcct tcagcagcag gtacatgctc acgtcgccct   660
```

```
tcaggatgcc ctgcttaggc acgggcatga tcttctcgca gctggcctcc cagttggtgg      720
tcatcttctt catcacgggg ccgtcggcgg ggaagttcac gccgttgaag atgctcttgt      780
ggtagatgca gttctccttc acgctcacgg tgatgtccac gttacagatg cacacggcgc      840
cgtcctcgaa caggaagctc cggcccagg  tgtagccggc ggggcagctg ttcttgaagt      900
agtccacgat gtcctggggg tactcggtga agatccggtc gccgtacttg aagccggcgc      960
tcaggatgtc ctcgctgaag gcagggggc  cgccctcgat cacgcacagg ttgatggtct     1020
gcttgccctt gaaggggtag ccgatgccct cgccggtgat cacgaacttg tggccgttca     1080
cgcagccctc catgtggtac ttcatggtca tctcctcctt caggccgtgc ttgctgtggg     1140
ccatggtggc gaccgtcgaa ttcgtgtgaa gtctaagaag atcaagaaga aagtctgaa      1200 gccgcgtagt gtcctgtact tgagggtctt atatactgac gaaggcccct tgctaattat     1260
agacccaacc ttaagtgagg tttgggaaat agcagaccga gagagaaaga ggaaaaacta     1320
tgaggtaggg ggaaagtgat ggagggacac cggctgggat gtactatcat cttacagtgc     1380
tcagaaatag ctattggagt cttggaatgg gatgaatctg atactgatgg cagcggcctg     1440
catgtctcgc gttgtctaat aaggacatgg ggacgtaagg gactgtttga gcttcataca     1500
atcacataac tcaatttgaa atgaatgagc tgtagccact gagtctaaag gggacgcaac     1560
tccctcccct aaagttagat tagcagcaga tcaatactgg cttatcttgc aggattactt     1620
gttggatggg gagggttgca gtgatagatc ctgatggatt tcaatccaga gattttttgag    1680 ccaatgatta tgttgttcat atttgttcac gccctggctg atatataaga ggacgttctg     1740
gtgtcttaac ccttatttca aatcagccct aatcgaaaat aggttttaat gcttttccta     1800
gtatagtgat gctgtaagat ttcggttcaa gtgccccac  cacacccgtc acatggcca      1860 tgcccatatt cagcactctc tctctctctc tctctctctc tctctgccga tcgacctatg     1920
acctcacccg gtcacttcag tgactgtgag gtgccatttg tgggaagctg ccctgtggac     1980
aagcacgtaa ttaccccttt tcccagtttt ttagatggtc agcacactac agccctctga     2040
gtggttgatg ttggacccct catgaagaga atttgaggct taagacagtt ttttttttggg    2100 aaggcaggca taaggaacag ctgtggtgac caaaatagct aaacaatctt gagcgctcct     2160
tgctctcttt tcttgtcta  attcatcagt cactgtttg  cccccctga  gtttgttgtg    2220 cattcccttc tttcttttaga ctaatttgat atcctgtgag tctgtcggct tgttttgctc    2280
ctgcttgttc caaaattgtt taagattagc attatttttac agtacctaga aaaacagata    2340
attacagtgc ttagagtaat tgagtacagc ccatttttgaa aatgaatatt tttctccatc    2400
tctcagtgaa tataggcaat gtatttttggt gcatttaaac aaaacagatt tattaaacag    2460
ctatatttat taaaaataata ttttagtcac aaaaattgaaa gataaaacaa tttaaataaa    2520
gctaaatatt gcaacaaaaa aattacaacc tacaaatttt gaactaattt ttttccattg     2580
ttttgcttct cttgatttt  ccctgtttat aaatttgtat ttaatattt  tcaataacat    2640 ataaatatgg gtgtagtagt ttttggaccg ttatcataag ttattttgtt aaataagctc     2700
cagatttagc ttcactctca gaaataaagg gcgtgagctg tcactggggt ggtacctttc     2760
caaatgataa aaatttgtac cttaaaggtc cataataaaa cctcaagggt atatattagt     2820
acctaaaaag tacaaaagtg tttctcttaa aattttttagg cactaatata acttttttgag   2880 gtatcaatat ggacccttta agtacaaata tgtacctttt gaaaaggtac caccgcagtg     2940
acagcttgcg gaccatttat ttctgagagt gtactgacta atctaatgta tatgcacaaa     3000
```

| | |
|---|---|
| tataacatag cttcctatta aaaatattaa tttaaaagac agatttgggt gtttcccagt | 3060 |
| gtagggttgc aactggatgg gcatccgctg cataaaaaat acactggatg agttggtggc | 3120 |
| tcattcctct gtggcgatcg ataccgtcga cct | 3153 |

<210> SEQ ID NO 5
<211> LENGTH: 3688
<212> TYPE: DNA
<213> ORGANISM: Artificial
<220> FEATURE:
<223> OTHER INFORMATION: Cloned expression cassette

<400> SEQUENCE: 5

| | |
|---|---|
| ctagaaccat gattacgcca agcttttaga ccttcttact tttggggatt atataagtat | 60 |
| tttctcaata aatatctcat atcttactgt ggtttaactg ctgaatctaa aattttaata | 120 |
| caaaagtagt tatatttgtt gtacattgta aactataact taacttcagt ttcagagaaa | 180 |
| ctcatgtgct caaaatgtaa aaaaagtttc ctgttaaata ttttgtaaat gtattgaaga | 240 |
| caaaataaga aaaaaaaaaa tataagccac taaatcacac tgtccttggt atcagcaaga | 300 |
| gattctgaca taatcagctg ttttttgttta ttactgccat tgaaggccat gtgcattagt | 360 |
| cccaagttac acattaaaaa gtcacatgta gcttaccaac atcagtgctg ttcaagcaca | 420 |
| gcctcatcta ctattcaaac tgtggcacca tctaaaatat gccagaattt ttttatttaa | 480 |
| tgaatttgac cctgaaatat gtattaatat cactcctgtg atttttttgt aatcagctta | 540 |
| caattacagg aatgcaagcc tgattcatta caagtttcac tacactttct ctgacaacat | 600 |
| cacctactga actcagacca gctagttgct ccttaagtat acaatcatgt cactaatcct | 660 |
| catttcaatg aaaaataccc ctattgtact tggtacttgg tagataacca cagagcagta | 720 |
| ttatgccatt attgtgaata caataagagg taaatgacct acagagctgc tgctgctgtt | 780 |
| gtgttagatt gtaaacacag cacaggatca aggaggtgtc catcactatg accaatacta | 840 |
| gcactttgca caggctcttt gaaaggctga aagagccttt attggcgtta tcacaacaaa | 900 |
| atacgcaaat acggaaaaca acgtattgaa cttcgcaaac aaaaaacagc gattttgatg | 960 |
| aaaatcgctt aggccttgct cttcaaacaa tccagcttct ccttctttca ctctcaagtt | 1020 |
| gcaagaagca agtgtagcaa tgtgcacgcg acagccgggt gtgtgacgct ggaccaatca | 1080 |
| gagcgcagag ctccgaaagt ttacctttta tggctagagc cggcatctgc cgtcatataa | 1140 |
| aagagcgcgc ccagcgtctc agcctcactt tgagctcctc cacacgcagc tagtgcggaa | 1200 |
| tatcatctgc ctgtaaccca ttctctaaag tcgacaaacc cccccaaacc taaggtgagt | 1260 |
| tgatctttaa gcttttttaca ttttcagctc gcatatatca attcgaacgt ttaattagaa | 1320 |
| tgtttaaata aagctagatt aaatgattag gctcagttac cggtcttttt tttctcattt | 1380 |
| acgtgcgaac tctgcttaaa ctctagttat tctttattaa tatgtggtta tttttatata | 1440 |
| tgtatgttat cataactgta ctggctatgt caggtggtaa tgactgtaac gttacgttac | 1500 |
| tcgttgtagg cacgacattg aatgggccgg tgttgaaata agtcttcaac cccttttaac | 1560 |
| ctcaaaatgt gctctggtta acaaggattt taacagctat cagtatgact gtgcggtttt | 1620 |
| aaagccgtta gtgaggcacg ttgcacactt gatggatggc cggaatggga agttctttat | 1680 |
| gcaggcagtg ctgcagcagg gtgtgaccta ctttagctaa cgttagccgg ctaaccagca | 1740 |
| ttcatctgcc ggtaacttga gtctaatatt ctctatgtga tatcgaagtg atcaaagaca | 1800 |
| cgtctgttag ctcactttaa ccaactgtag tgaaaaatag cgcagtgtgc agcccttcaa | 1860 |
| gtctttcatt taggctgatt attcaatcat tttattaact attaacgcgt tactaaacgt | 1920 |

```
aaggtaacgt agtcagtttt taataactgg tgaaaagtac tggttgggtt taaatggtga    1980
cttataattg tgttggaggg ggaaaccttt ttgataaagg ctatataatc tcaaatgaat    2040
gggctgagga tggtgttcac aggtgcttta gtgaagtccg ctcgtgaaga gtcgctgaag    2100
tgactgcaga tctgtagcgc atgcgttttg gcagacggcc gttgaaattc ggttgagtaa    2160
ttgataccag gtgaggctag aggatgtaga aattcatttg tgtagaattt agggagtggc    2220
ctggcgtgat gaatgtcgaa atccgttcct ttttactgaa ccctatgtct ctgctgagtg    2280
ccacaccgcc ggcacaaagc gtctcaaacc attgccttt atggtaataa tgagaatgca    2340
gagggacttc ctttgtctgg cacatctgag gcgcgcattg tcacactagc acccactagc    2400
ggtcagactg cagacaaaca ggaagctgac tccacatggt cacatgctca ctgaagtgtt    2460
gacttccctg acagctgtgc actttctaaa ccggttttct cattcattta cagttcagcc    2520
gggtaccgaa ttcgacggtc gccaccatgg cccagtccaa gcacggcctg accaaggaga    2580
tgaccatgaa gtaccgcatg gagggctgcg tggacggcca caagttcgtg atcaccggcg    2640
agggcatcgg ctacccttc aagggcaagc aggccatcaa cctgtgcgtg gtggagggcg    2700
gccccttgcc cttcgccgag gacatcttgt ccgccgcctt catgtacggc aaccgcgtgt    2760
tcaccgagta cccccaggac atcgtcgact acttcaagaa ctcctgcccc gccggctaca    2820
cctgggaccg ctccttcctg ttcgaggacg gcgccgtgtg catctgcaac gccgacatca    2880
ccgtgagcgt ggaggagaac tgcatgtacc acgagtccaa gttctacggc gtgaacttcc    2940
ccgccgacgg ccccgtgatg aagaagatga ccgacaactg ggagccctcc tgcgagaaga    3000 tcatcccgt gcccaagcag ggcatcttga agggcgacgt gagcatgtac ctgctgctga    3060
aggacggtgg ccgcttgcgc tgccagttcg acaccgtgta caaggccaag tccgtgcccc    3120
gcaagatgcc cgactggcac ttcatccagc acaagctgac ccgcgaggac cgcagcgacg    3180
ccaagaacca gaagtggcac ctgaccgagc acgccatcgc ctccggctcc gccttgccct    3240
gagactagtg atccagagtt cattgatgag tttggacaaa ccacaactag aatgcagtga    3300
aaaaaatgct ttatttgtga aatttgtgat gctattgctt tatttgtaac cattataagc    3360
tgcaataaac aagttaacaa caacaattgc attcatttta tgtttcaggt tcaggggggag   3420 atgtgggagg ttttttaaag caagtaaaac ctctacaaat gtggtcattg atgagtttgg    3480
acaaaccaca actagaatgc agtgaaaaaa atgctttatt tgtgaaattt gtgatgctat    3540
tgctttattt gtaaccatta taagctgcaa taaacaagtt aacaacaaca attgcattca    3600
ttttatgttt caggttcagg gggagatgtg ggaggttttt taaagcaagt aaaacctcta    3660
caaatgtggt cattccgctg ttgacgtc                                       3688
```